(12) United States Patent
Meazza et al.

(10) Patent No.: US 7,754,880 B2
(45) Date of Patent: Jul. 13, 2010

(54) URACILS HAVING A HERBICIDAL ACTIVITY

(75) Inventors: Giovanni Meazza, Saronno-Varese (IT); Piero Paravidino, Sedriano-Milano (IT); Franco Bettarini, Novara (IT); Luca Fornara, Cerro Al Lambro-Milano (IT)

(73) Assignee: Isagro Ricerca S.r.l., Milan (IT)

( * ) Notice: Subject to any disclaimer, the term of this patent is extended or adjusted under 35 U.S.C. 154(b) by 986 days.

(21) Appl. No.: 10/536,485

(22) PCT Filed: Dec. 15, 2003

(86) PCT No.: PCT/EP03/14469

§ 371 (c)(1), (2), (4) Date: May 24, 2005

(87) PCT Pub. No.: WO2004/056785

PCT Pub. Date: Jul. 8, 2004

(65) Prior Publication Data

US 2006/0025591 A1   Feb. 2, 2006

(30) Foreign Application Priority Data

Dec. 23, 2002   (IT) .......................... MI2002A2758

(51) Int. Cl.
  *C07D 403/00* (2006.01)
  *C07D 239/02* (2006.01)
(52) U.S. Cl. ..................................... 544/298
(58) Field of Classification Search ....................... None
See application file for complete search history.

(56) References Cited

U.S. PATENT DOCUMENTS 4,812,164 A * 3/1989 Wenger et al. ............. 504/243
4,859,229 A * 8/1989 Wenger et al. ............. 504/243
5,084,084 A   1/1992 Satow et al.
6,258,751 B1 * 7/2001 Jacobson et al. ........... 504/227

FOREIGN PATENT DOCUMENTS

| CN | 1327984 | * | 6/2000 |
| EP | 0255047 | * | 2/1988 |
| EP | 0 563 384 | | 10/1993 |
| EP | 1 061 075 | | 12/2000 |
| EP | 1 122 244 | | 8/2001 |
| EP | 1122244 | * | 8/2001 |
| WO | WO 98/27067 | | 6/1998 |
| WO | WO 01/77084 | | 10/2001 |
| WO | WO 03/099009 | | 12/2003 |

OTHER PUBLICATIONS

Borisy, et. al., Proceedings of the National Academy of Sciences of the United States of America, 100(13) 7977-7982.*

* cited by examiner

*Primary Examiner*—James O Wilson
*Assistant Examiner*—Jeffrey H Murray
(74) *Attorney, Agent, or Firm*—Hedman & Costigan, P.C.; James V. Costigan

(57) ABSTRACT

New uracils are described, having general formula (I) and their use as herbicides.

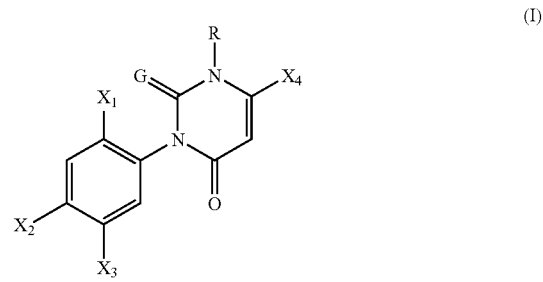

(I)

6 Claims, No Drawings

URACILS HAVING A HERBICIDAL ACTIVITY

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISK

Not Applicable

REFERENCE TO A MICROFICHE APPENDIX

Not Applicable

BACKGROUND OF THE INVENTION

1 Field of the Invention

The present invention relates to new uracils.

More specifically, the present invention relates to new uracils having a high herbicidal activity, the processes for their preparation and methods for their use as herbicides for controlling weeds in agricultural crops.

2 Description of Related Art

Uracils having a herbicidal activity are described, among others, in patents or patent applications U.S. Pat. No. 4,859,229, U.S. Pat. No. 5,084,084, EP 1122244 and WO 01/77084.

BRIEF SUMMARY OF THE INVENTION

The Applicant has now surprisingly found uracils which, compared to the products described in the above patents or patent applications, show enhanced characteristics in terms of herbicidal activity with respect to weeds and/or in terms of a lower phytotoxicity for crops of agricultural interest.

DETAILED DESCRIPTION OF THE INVENTION

The object of the present invention therefore relates to new uracils having general formula (I):

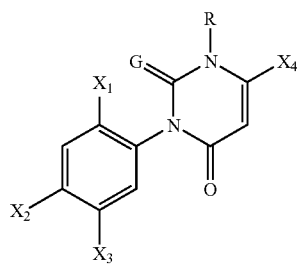

wherein:
$X_1$ represents a hydrogen atom or a halogen atom;
$X_2$ represents a halogen atom;
$X_4$ represents a $C_1$-$C_3$ haloalkyl group;
R represents a hydrogen atom, a $C_1$-$C_3$ alkyl group or a $C_1$-$C_3$ haloalkyl group;
G represents an oxygen atom or a sulphur atom;
$X_3$ represents a $Q(CR_1R_2)_nZ$— group, a $Q_1Z$ group, a $Q_2$- group, a Y(OC)—$CR_6$=$CR_5$—$CR_3R_4Z$— group;
Z represents an oxygen atom or a sulphur atom;
$R_1$, $R_2$, $R_3$ and $R_4$, the same or different, represent a hydrogen atom, a $C_1$-$C_4$ alkyl group or a $C_1$-$C_4$ haloalkyl group;
$R_5$ represents an $OR_7$ group;
$R_6$ represents a hydrogen atom or a $C_1$-$C_4$ alkyl group;
$R_7$ represents a $C_1$-$C_4$ alkyl group or a $C_1$-$C_4$ haloalkyl group;
Y represents an $OR_8$ group, a $SR_9$ group, a $NR_{10}R_{11}$ group;
$R_8$ and $R_9$ represent a hydrogen atom, a $C_1$-$C_6$ linear or branched alkyl group, a $C_1$-$C_6$ linear or branched haloalkyl group, a $C_3$-$C_6$ cycloalkyl group, a $C_4$-$C_9$ cycloalkylalkyl group, a $C_3$-$C_6$ cyanoalkyl group, a $C_3$-$C_6$ alkoxyalkyl group, an oxethanyl group, a tetrahydrofuranyl group; a phenyl group, a $C_7$-$C_{12}$ phenylalkyl group, a pyridyl group, said groups, in turn, possibly substituted with one or more halogen atoms selected from chlorine, fluorine, bromine or iodine, or substituted with one or more groups selected from $C_1$-$C_4$ alkyl, or $C_1$-$C_4$ haloalkyl, $C_1$-$C_4$ alkoxy or $C_1$-$C_4$ haloalkoxy;
$R_{10}$ and $R_{11}$, the same or different, represent a hydrogen atom, or a $C_1$-$C_6$ alkyl group, a $C_1$-$C_6$ haloalkyl group, a $C_3$-$C_6$ cycloalkyl group, a $C_7$-$C_{12}$ arylalkyl group, or an aryl group, said groups, in turn, possibly substituted with one or more halogen atoms selected from chlorine, fluorine, bromine or iodine, or substituted with one or more groups selected from a $C_1$-$C_4$ alkyl, or $C_1$-$C_4$ haloalkyl, $C_1$-$C_4$ alkoxy or $C_1$-$C_4$ haloalkoxy; or, jointly represent a $C_2$-$C_7$ alkylene chain possibly substituted with $C_1$-$C_4$ alkyl groups and possibly interrupted by oxygen atoms or by a $NR_{12}$ group, wherein:
$R_{12}$ represents a hydrogen atom, a $C_1$-$C_6$ alkyl group or $C_1$-$C_6$ haloalkyl group, a $C_3$-$C_6$ alkenyl group or a $C_3$-$C_6$ haloalkenyl group, a $C_3$-$C_6$ alkynyl group or $C_3$-$C_6$ haloalkynyl group, a $C_2$-$C_8$ alkoxyalkyl group or a $C_2$-$C_8$ haloalkoxyalkyl group, a $C_2$-$C_7$ alkylcarbonyl group or $C_2$-$C_7$ haloalkylcarbonyl group:
n represents 1, 2 or 3;
Q represents a heterocyclic group selected from pyrrol-2-yl, pyrrol-3-yl, imidazol-2-yl, imidazol-4-yl, imidazol-5-yl, pyrazol-3-yl, pyrazol-4-yl, pyrazol-5-yl, 1,2,4-triazol-3-yl, 1,2,4-triazol-5-yl, 1,2,4-triazol-3-onyl, 1,2,3-triazolyl, tetrazolyl, oxazolyl, isoxazol-5-yl, thiazol-2-yl, thiazol-5-yl, isothiazolyl, 1,3,4-oxadiazolyl, 1,3,4-thiadiazolyl, 1,2,4-thiadiazolyl, 1,2,4-oxadiazolyl, 1,2,4-oxadiazol-5-on-3-yl, benzoxazol-2-yl, benzothiazol-2-yl, pyrazinyl, pyridazinyl, 1,2,4-triazinyl, 1,3,4-thiadiazol-2-on-5-yl, 1,4,2-dioxazol-5-on-3-yl, 1,4,2-oxathiazol-5-on-3-yl, 1,3,4-oxadiazin-5-on-2-yl, 1,4,2-dioxazin-3-yl, 1,2,4-oxadiazin-5-on-3-yl, 4, 5, 6, 7-tetrahydro-1,3-benzothiazol-2-yl, 5,6-dihydro-4H-cyclopenta[d][1,3]thiazole, said groups, in turn, possibly substituted with halogen atoms selected from chlorine, fluorine, bromine or iodine, or substituted with groups selected from $C_1$-$C_6$ alkyl or $C_1$-$C_6$ haloalkyl, $C_2$-$C_6$ alkenyl or $C_2$-$C_6$ halo-alkenyl, $C_2$-$C_6$ alkenyloxy or $C_2$-$C_6$ haloalkenyloxy, $C_2$-$C_6$ alkynyl or $C_2$-$C_6$ haloalkynyl, $C_2$-$C_6$ alkynyloxy or $C_2$-$C_6$ haloalkynyloxy, $C_1$-$C_6$ alkoxy or $C_1$-$C_6$ haloalkoxy, $C_2$-$C_6$ alkoxyalkyl or $C_2$-$C_6$ haloalkoxyalkyl, $C_2$-$C_6$ alkoxyalkoxy, $C_2$-$C_6$ haloalkoxyalkoxy, $C_2$-$C_6$ haloalkoxyhaloalkoxy, $C_3$-$C_8$ alkoxyalkoxyalkyl, $C_3$-$C_8$ alkoxyalkoxyalkoxy, $C_1$-$C_6$ alkylthio or $C_1$-$C_6$ haloalkylthio, $C_2$-$C_6$ alkylthioalkyl, $C_1$-$C_6$ alkylsulfinic or $C_1$-$C_6$ haloalkylsulfinic, $C_1$-$C_6$ alkylsulfonic or $C_1$-$C_6$ haloalkylsulfonic, $C_2$-$C_6$ alkoxycarbonyl or $C_2$-$C_6$ haloalkoxycarbonyl, $C_3$-$C_7$ alkenyloxycarbonyl or $C_3$-$C_7$ alkynyloxycarbonyl, $C_3$-$C_8$ alkoxycarbonylalkyl or $C_3$-$C_8$ haloalkoxycarbonylalkyl, $C_4$-$C_9$ alkenyloxycarbonylalkyl or $C_4$-$C_9$ alkynyloxycarbonylalkyl, $C_3$-$C_7$ alkoxycarbonylalkoxy, $C_4$-$C_9$ alkenyloxycarbonylalkoxy or $C_4$-$C_9$ alkynyloxycarbonylalkoxy, $C_3$-$C_8$ aminocarbonylalkoxy possibly substituted with $C_1$-$C_4$ alkyl groups or with a $C_2$-$C_5$ alkylene group; CN, CHO, $NO_2$, $NH_2$, OH, $C_1$-$C_3$ cyanoalkyl, $C_1$-$C_3$ cyanoalkyloxy, $C_2$-$C_6$ formylalkyl, $C_2$-$C_6$ alkylcarbonyl, $C_2$-$C_6$ haloalkylcarbonyl, $C_3$-$C_7$ alkylcarbonylalkyl, $C_2$-$C_6$ alkoxyimino, $C_2$-$C_6$ haloalkoxyimino, $C_3$-$C_6$ alkoxyiminoalkyl, $C_3$-$C_6$ haloalkoxyiminoalkyl, $C_3$-$C_6$ alkoxyiminohaloalkyl, aminocarbonyl, $C_2$-$C_6$ aminocarbonylalkyl, aminosulfonyl or $C_2$-$C_6$ aminosulfonylalkyl, these last four groups possibly substituted with one or two $C_1$-$C_4$ alkyl groups or with a $C_2$-$C_5$ alkylene group; $C_1$-$C_6$ alkylsulfonylamino, $C_2$-$C_7$ alkylcarbonylamino or $C_2$-$C_7$ alkoxycarbonylamino, these last three groups possibly substituted with $C_1$-$C_4$ alkyl groups; $C_6$-$C_{10}$ aryl, $C_6$-$C_{12}$ arylalkyl, $C_6$-$C_{10}$ arylalkoxy, $C_7$-$C_{12}$ aryloxyalkyl, $C_8$-$C_{12}$ arylalkyloxyalkyl said groups in turn possibly substituted with halogen atoms, $C_1$-$C_4$ alkyl groups, $C_1$-$C_3$ haloalkyl groups, $C_1$-$C_4$ alkoxy groups, $C_1$-$C_3$ haloalkoxy groups, CN; $C_3$-$C_7$ cycloalkyl, $C_6$-$C_{12}$ cycloalkylalkyl, $C_6$-$C_{10}$ cycloalkylalkoxy, tetrahydropyran-2-yl said groups in turn possibly substituted with halogen atoms, $C_1$-$C_4$ alkyl groups, $C_1$-$C_4$ alkoxy groups;

$Q_1$ represents a heterocyclic group selected from 1,3,4-thiadiazol-2-yl, 1,3,4-thiadiazol-5-yl, 1,2,4-thiadiazol-5-yl, tetrazol-5-yl, 1,3,4-oxadiazol-2-yl, 1,3,4-oxadiazol-5-yl, 1,2,4-oxadiazol-5-yl, oxazol-2-yl, oxazol-4-yl, oxazol-5-yl, isoxazol-3-yl, isoxazol-5-yl, thiazol-2-yl, thiazol-4-yl, thiazol-5-yl, said groups, in turn, possibly substituted with halogen atoms selected from chlorine, fluorine, bromine or iodine, or substituted with groups selected from $C_1$-$C_6$ alkyl or $C_1$-$C_6$ haloalkyl, $C_2$-$C_6$ alkenyl or $C_2$-$C_6$ haloalkenyl, $C_2$-$C_6$ alkenyloxy or $C_2$-$C_6$ haloalkenyloxy, $C_2$-$C_6$ alkynyl or $C_2$-$C_6$ haloalkynyl, $C_2$-$C_6$ alkynyloxy or $C_2$-$C_6$ haloalkynyloxy, $C_1$-$C_6$ alkoxy or $C_1$-$C_6$ haloalkoxy, $C_2$-$C_6$ alkoxyalkyl or $C_2$-$C_6$ haloalkoxyalkyl, $C_1$-$C_6$ alkylthio or $C_1$-$C_6$ haloalkylthio, $C_1$-$C_6$ alkylsulfinic or $C_1$-$C_6$ haloalkylsulfinic, $C_1$-$C_6$ alkylsulfonic or $C_1$-$C_6$ haloalkylsulfonic, $C_2$-$C_6$ alkoxycarbonyl or $C_2$-$C_6$ haloalkoxycarbonyl, $C_3$-$C_8$ alkoxycarbonylalkyl or $C_3$-$C_8$ haloalkoxycarbonylalkyl, $C_3$-$C_8$ alkoxycarbonylalkoxy, $C_3$-$C_8$ aminocarbonylalkoxy possibly substituted with $C_1$-$C_4$ alkyl groups or with a $C_2$-$C_6$ alkylene; CN, CHO, $NO_2$, $NH_2$, $C_1$-$C_3$ cyanoalkyl, $C_1$-$C_3$ cyanoalkyloxy, $C_2$-$C_6$ alkylcarbonyl, $C_2$-$C_6$ haloalkylcarbonyl, $C_3$-$C_6$ alkoxyiminoalkyl, $C_3$-$C_6$ haloalkoxyiminoalkyl, aminocarbonyl, $C_2$-$C_6$ aminocarbonylalkyl, aminosulfonyl or $C_2$-$C_6$ aminosulfonylalkyl, these last four groups possibly substituted with one or two $C_1$-$C_4$ alkyl groups or with a $C_2$-$C_5$ alkylene; $C_1$-$C_6$ alkylsulfonylamino, $C_2$-$C_7$ alkylcarbonylamino or $C_2$-$C_7$ alkoxycarbonylamino, these last three groups possibly substituted with $C_1$-$C_4$ alkyl groups; $C_6$-$C_{10}$ aryl, $C_6$-$C_{12}$ arylalkyl, $C_6$-$C_{10}$ arylalkoxy, $C_7$-$C_{12}$ aryloxyalkyl, $C_8$-$C_{12}$ arylalkyloxyalkyl said groups in turn possibly substituted with halogen atoms, $C_1$-$C_4$ alkyl groups, $C_1$-$C_3$ haloalkyl groups, $C_1$-$C_4$ alkoxy groups, $C_1$-$C_3$ haloalkoxy groups, CN; $C_3$-$C_7$ cycloalkyl, $C_6$-$C_{12}$ cycloalkylalkyl, $C_6$-$C_{10}$ cycloalkylalkoxy, tetrahydropyran-2-yl said groups in turn possibly substituted with halogen atoms, $C_1$-$C_4$ alkyl groups, $C_1$-$C_4$ alkoxy groups;

$Q_2$ represents a heterocyclic group selected from tetrazol-5-yl, thiazol-2-yl, thiazol-4-yl, thiazol-5-yl, isothiazol-3-yl, isothiazol-4-yl, isothiazol-5-yl, 1,2,3-triazolyl, benzoxazol-2-yl, benzothiazol-2-yl, pyrimidin-2-yl, 1,2,4-triazinyl, 1,3,5-triazinyl, 1,3,4-thiadiazol-2-on-5-yl, 1,4,2-dioxazol-5-on-3-yl, 1,4,2-oxathiazol-5-on-3-yl, 1,3,4-oxadiazin-5-on-2-yl, 1,4,2-dioxazin-3-yl, 1,2,4-oxadiazin-5-on-3-yl, 4,5,6,7-tetrahydro-1,3-benzothiazol-2-yl, 5,6-dihydro-4H-cyclopenta[d][1,3]thiazole, said groups in turn possibly substituted with halogen atoms selected from chlorine, fluorine, bromine or iodine, or substituted with groups selected from $C_1$-$C_6$ alkyl or $C_1$-$C_6$ haloalkyl, $C_2$-$C_6$ alkenyl or $C_2$-$C_6$ haloalkenyl, $C_2$-$C_6$ alkenyloxy or $C_2$-$C_6$ haloalkenyloxy, $C_2$-$C_6$ alkynyl or $C_2$-$C_6$ haloalkynyl, $C_2$-$C_6$ alkynyloxy or $C_2$-$C_6$ haloalkynyloxy, $C_1$-$C_6$ alkoxy or $C_1$-$C_6$ haloalkoxy, $C_2$-$C_6$ alkoxyalkyl or $C_2$-$C_6$ haloalkoxyalkyl, $C_2$-$C_6$ alkoxyalkoxy, $C_2$-$C_6$ haloalkoxyalkoxy, $C_2$-$C_6$ haloalkoxyhaloalkoxy, $C_3$-$C_8$ alkoxyalkoxyalkyl, $C_3$-$C_8$ alkoxyalkoxyalkoxy, $C_1$-$C_6$ alkylthio or $C_1$-$C_6$ haloalkylthio, $C_2$-$C_6$ alkylthioalkyl, $C_1$-$C_6$ alkylsulfinic or $C_1$-$C_6$ haloalkylsulfinic, $C_1$-$C_6$ alkylsulfonic or $C_1$-$C_6$ haloalkylsulfonic, $C_2$-$C_6$ alkoxycarbonyl or $C_2$-$C_6$ haloalkoxycarbonyl, $C_3$-$C_7$ alkenyloxycarbonyl or $C_3$-$C_7$ alkynyloxycarbonyl, $C_3$-$C_8$ alkoxycarbonylalkyl or $C_3$-$C_8$ haloalkoxycarbonylalkyl, $C_4$-$C_9$ alkenyloxycarbonylalkyl or $C_4$-$C_9$ alkynyloxycarbonylalkyl, $C_3$-$C_8$ alkoxycarbonylalkoxy, alkenyloxycarbonylalkoxy $C_4$-$C_9$ or alkynyloxycarbonylalkoxy $C_4$-$C_9$, $C_3$-$C_8$ aminocarbonylalkoxy possibly substituted with $C_1$-$C_4$ alkyl or with a $C_2$-$C_5$ alkylene; CN, CHO, $NO_2$, $NH_2$, OH, $C_1$-$C_3$ cyanoalkyl, $C_1$-$C_3$ cyanoalkyloxy, $C_2$-$C_6$ formylalkyl, $C_2$-$C_6$ alkylcarbonyl, $C_2$-$C_6$ haloalkylcarbonyl, $C_3$-$C_7$ alkylcarbonylalkyl, $C_2$-$C_6$ alkoxyimino, $C_2$-$C_6$ haloalkoxyimino, $C_3$-$C_6$ alkoxyiminoalkyl, $C_3$-$C_6$ haloalkoxyiminoalkyl, alkoxyiminohaloalkyl $C_3$-$C_6$, aminocarbonyl, $C_2$-$C_6$ aminocarbonylalkyl, aminosulfonyl or $C_2$-$C_6$ aminosulfonylalkyl, these last four groups possibly substituted with one or two $C_1$-$C_4$ alkyl groups or with a $C_2$-$C_5$ alkylene; $C_1$-$C_6$ alkylsulfonylamino, $C_2$-$C_7$ alkylcarbonylamino o $C_2$-$C_7$ alkoxycarbonylamino, these last three groups possibly substituted with $C_1$-$C_4$ alkyl groups; $C_6$-$C_{10}$ aryl, $C_6$-$C_{12}$ arylalkyl, $C_6$-$C_{10}$ arylalkoxy, $C_7$-$C_{12}$ aryloxyalkyl, $C_8$-$C_{12}$ arylalkyloxyalkyl said groups in turn possibly substituted with halogen atoms, $C_1$-$C_4$ alkyl groups, $C_1$-$C_3$ haloalkyl groups, $C_1$-$C_4$ alkoxy groups, $C_1$-$C_3$ haloalkoxy groups, CN; $C_3$-$C_7$ cycloalkyl, $C_6$-$C_{12}$ cycloalkylalkyl, $C_6$-$C_{10}$ cycloalkylalkoxy, tetrahydropyran-2-yl said groups in turn possibly substituted with halogen atoms, $C_1$-$C_4$ alkyl groups, $C_1$-$C_4$ alkoxy groups.

A further object of the present invention relates to the use of uracils having general formula (I), as herbicides.

Specific examples of compounds having general formula (I) which are interesting for their high herbicidal activity are:

methyl (2E)-4-{2-chloro-4-fluoro-5-[1,2,3,6-tetrahydro-3-methyl-2,6-dioxo-4-(trifluoromethyl)pyrimidin-1-yl]phenoxy}-3-methoxybut-2-enoate;

methyl (2E)-4-{2,4-dichloro-5-[1,2,3,6-tetrahydro-3-methyl-2,6-dioxo-4-(trifluoromethyl)pyrimidin-1-yl]phenoxy}-3-methoxybut-2-enoate;

methyl (2E)-4-{2-chloro-4-fluoro-5-[1,2,3,6-tetrahydro-3-methyl-2,6-dioxo-4-(trifluoromethyl)pyrimidin-1-yl]phenylthio}-3-methoxybut-2-enoate;
ethyl (2E)-4-{2-chloro-4-fluoro-5-[1,2,3,6-tetrahydro-3-methyl-2,6-dioxo-4-(trifluoromethyl)pyrimidin-1-yl]phenoxy}-3-ethoxybut-2-enoate;
methyl (2E)-4-{2,4-dichloro-5-[1,2,3,6-tetrahydro-3-methyl-2,6-dioxo-4-(trifluoromethyl)pyrimidin-1-yl]phenylthio}-3-methoxybut-2-enoate;
ethyl (2E)-4-{2,4-dichloro-5-[1, 2, 3, 6-tetrahydro-3-methyl-2,6-dioxo-4-(trifluoromethyl)pyrimidin-1-yl]phenoxy}-3-ethoxybut-2-enoate;
isopropyl (2E)-4-{2-chloro-4-fluoro-5-[1,2,3,6-tetrahydro-3-methyl-2,6-dioxo-4-(trifluoromethyl)pyrimidin-1-yl]phenoxy}-3-methoxybut-2-enoate;
methyl (2E)-4-{2-chloro-4-fluoro-5-[1,2,3,6-tetrahydro-2,6-dioxo-4-(trifluoromethyl)pyrimidin-1-yl]phenoxy}-3-methoxybut-2-enoate;
methyl (2E)-4-{2,4-dichloro-5-[1,2,3,6-tetrahydro-2,6-dioxo-4-(trifluoromethyl)pyrimidin-1-yl]phenoxy}-3-methoxybut-2-enoate;
ethyl (2E)-4-{2-chloro-4-fluoro-5-[1,2,3,6-tetrahydro-2,6-dioxo-4-(trifluoromethyl)pyrimidin-1-yl]phenoxy}-3-ethoxybut-2-enoate;
ethyl (2E)-4-{2,4-dichloro-5-[1,2,3,6-tetrahydro-2,6-dioxo-4-(trifluoromethyl)pyrimidin-1-yl]phenoxy}-3-ethoxybut-2-enoate;
2,2,2-trifluoroethyl (2E)-4-{2-chloro-4-fluoro-5-[1,2,3,6-tetrahydro-2,6-dioxo-4-(trifluoromethyl)pyrimidin-1-yl]phenoxy}-3-methoxybut-2-enoate;
(2E)-4-{2-chloro-4-fluoro-5-[1,2,3,6-tetrahydro-2,6-dioxo-4-(trifluoromethyl)pyrimidin-1-yl]phenoxy}-3-methoxy-N,N-dimethylbut-2-enamide;
S-ethyl (2E)-4-{2-chloro-4-fluoro-5-[1,2,3,6-tetrahydro-2,6-dioxo-4-(trifluoromethyl)pyrimidin-1-yl]phenoxy}-3-methoxybut-2-enethioate;
isopropyl (2E)-4-{2,4-dichloro-5-[1,2,3,6-tetrahydro-3-methyl-2,6-dioxo-4-(trifluoromethyl)pyrimidin-1-yl]phenoxy}-3-methoxybut-2-enoate;
2,2,2-trifluoroethyl (2E)-4-{2-chloro-4-fluoro-5-[1,2,3,6-tetrahydro-3-methyl-2,6-dioxo-4-(trifluoromethyl)pyrimidin-1-yl]phenoxy}-3-methoxybut-2-enoate;
2,2,2-trifluoroethyl (2E)-4-{2,4-dichloro-5-[1,2,3,6-tetrahydro-3-methyl-2,6-dioxo-4-(trifluoromethyl) pyrimidin-1-yl]phenoxy}-3-methoxybut-2-enoate;
S-ethyl (2E)-4-{2-chloro-4-fluoro-5-[1,2,3,6-tetrahydro-3-methyl-2,6-dioxo-4-(trifluoromethyl) pyrimidin-1-yl]phenoxy}-3-methoxybut-2-enethioate;
S-ethyl (2E)-4-{2,4-dichloro-5-[1,2,3,6-tetrahydro-3-methyl-2,6-dioxo-4-(trifluoromethyl)pyrimidin-1-yl]phenoxy}-3-methoxybut-2-enethioate;
(2E)-4-{2-chloro-4-fluoro-5-[1,2,3,6-tetrahydro-3-methyl-2,6-dioxo-4-(trifluoromethyl)pyrimidin-1-yl]phenoxy}-3-methoxy-N,N-dimethylbut-2-enamide;
(2E)-4-{2,4-dichloro-5-[1,2,3,6-tetrahydro-3-methyl-2,6-dioxo-4-(trifluoromethyl)pyrimidin-1-yl]phenoxy}-3-methoxy-N,N-dimethylbut-2-enamide;
(2E)-4-{2-chloro-4-fluoro-5-[1,2,3,6-tetrahydro-3-methyl-2,6-dioxo-4-(trifluoromethyl)pyrimidin-1-yl]phenylthio}-3-methoxy-N,N-dimethylbut-2-enamide;
(2E)-4-{2,4-dichloro-5-[1,2,3,6-tetrahydro-3-methyl-2,6-dioxo-4-(trifluoromethyl)pyrimidin-1-yl]phenylthio}-3-methoxy-N,N-dimethylbut-2-enamide;
3-[4-chloro-2-fluoro-5-(tetrazol-5-ylmethoxy)phenyl]-6-(trifluoromethyl)-2,4(1H,3H)-pyrimidinedione;
3-{4-chloro-2-fluoro-5-[(2-methyl-2H-tetrazol-5-yl)methoxy]phenyl}-6-(trifluoromethyl)-2,4(1H,3H)-pyrimidinedione;
3-[4-chloro-2-fluoro-5-(tetrazol-5-ylmethoxy)phenyl]-1-methyl-6-(trifluoromethyl)-2,4(1H,3H)-pyrimidinedione;
3-[2,4-dichloro-5-(tetrazol-5-ylmethoxy)phenyl]-1-methyl-6-(trifluoromethyl)-2,4(1H,3H)-pyrimidinedione;
3-{4-chloro-2-fluoro-5-[(2-methyl-2H-tetrazol-5-yl)methoxy]phenyl}-1-methyl-6-(trifluoromethyl)-2,4(1H,3H)-pyrimidinedione;
3-{4-chloro-2-fluoro-5-[(2-ethyl-2H-tetrazol-5-yl)methoxy]phenyl}-1-methyl-6-(trifluoromethyl)-2,4(1H,3H)-pyrimidinedione;
3-{2,4-dichloro-5-[(2-methyl-2H-tetrazol-5-yl)methoxy]phenyl}-1-methyl-6-(trifluoromethyl)-2,4(1H,3H)-pyrimidinedione;
3-{2,4-dichloro-5-[(2-ethyl-2H-tetrazol-5-yl)methoxy]phenyl}-1-methyl-6-(trifluoromethyl)-2,4(1H,3H)-pyrimidinedione;
3-{4-chloro-2-fluoro-5-[(1-ethyl-1H-tetrazol-5-yl)methoxy]phenyl}-1-methyl-6-(trifluoromethyl)-2,4(1H,3H)-pyrimidinedione;
3-{2,4-dichloro-5-[(1-ethyl-1H-tetrazol-5-yl)methoxy]phenyl}-1-methyl-6-(trifluoromethyl)-2,4(1H,3H)-pyrimidinedione;
3-{5-[(5-tert-butyl-1,3,4-oxadiazol-2-yl)methoxy]-4-chloro-2-fluorophenyl}-1-methyl-6-(trifluoromethyl)-2,4(1H,3H)-pyrimidinedione;
methyl [5-({2-chloro-4-fluoro-5-[1,2,3,6-tetrahydro-3-methyl-2,6-dioxo-4-(trifluoromethyl)pyrimidin-1-yl]phenoxy}methyl)-1H-tetrazol-1-yl]acetate;
methyl [5-({2,4-dichloro-5-[1,2,3,6-tetrahydro-3-methyl-2,6-dioxo-4-(trifluoromethyl)pyrimidin-1-yl]phenoxy}methyl)-1H-tetrazol-1-yl]acetate;
methyl [5-({2-chloro-4-fluoro-5-[1,2,3,6-tetrahydro-3-methyl-2,6-dioxo-4-(trifluoromethyl)pyrimidin-1-yl]phenoxy}methyl)-2H-tetrazol-2-yl]acetate;
methyl [5-({2,4-dichloro-5-[1,2,3,6-tetrahydro-3-methyl-2,6-dioxo-4-(trifluoromethyl)pyrimidin-1-yl]phenoxy}methyl)-2H-tetrazol-2-yl]acetate;
3-[4-chloro-3-(tetrazol-5-yl)phenyl]-6-(trifluoromethyl)-2,4(1H,3H)-pyrimidinedione;
3-[4-chloro-3-(2-methyl-2H-tetrazol-5-yl)phenyl]-6-(trifluoromethyl)-2,4(1H,3H)-pyrimidinedione;
3-[4-chloro-3-(1-methyl-1H-tetrazol-5-yl)phenyl]-6-(trifluoromethyl)-2,4(1H,3H)-pyrimidinedione;
3-[4-chloro-3-(tetrazol-5-yl)phenyl]-1-methyl-6-(trifluoromethyl)-2,4(1H,3H)-pyrimidinedione;
3-[4-chloro-2-fluoro-5-(tetrazol-5-yl)phenyl]-6-(trifluoromethyl)-2,4(1H,3H)-pyrimidinedione;
3-[2,4-dichloro-5-(tetrazol-5-yl)phenyl]-6-(trifluoromethyl)-2,4(1H,3H)-pyrimidinedione;
3-[4-chloro-2-fluoro-5-(tetrazol-5-yl)phenyl]-1-methyl-6-(trifluoromethyl)-2,4(1H,3H)-pyrimidinedione;
3-[2,4-dichloro-5-(tetrazol-5-yl)phenyl]-1-methyl-6-(trifluoromethyl)-2,4(1H,3H)-pyrimidinedione;
3-[4-chloro-3-(2-methyl-2H-tetrazol-5-yl)phenyl]-1-methyl-6-(trifluoromethyl)-2,4(1H,3H)-pyrimidinedione;
3-[4-chloro-2-fluoro-5-(2-methyl-2H-tetrazol-5-yl)phenyl]-6-(trifluoromethyl)-2,4(1H,3H)-pyrimidinedione;
3-[2,4-dichloro-5-(2-methyl-2H-tetrazol-5-yl)phenyl]-6-(trifluoromethyl)-2,4(1H,3H)-pyrimidinedione;
3-[4-chloro-2-fluoro-5-(1-methyl-1H-tetrazol-5-yl)phenyl]-6-(trifluoromethyl)-2,4(1H,3H)-pyrimidinedione;
3-[2,4-dichloro-5-(1-methyl-1H-tetrazol-5-yl)phenyl]-6-(trifluoromethyl)-2,4(1H,3H)-pyrimidinedione;

3-[4-chloro-2-fluoro-5-(2-methyl-2H-tetrazol-5-yl)phenyl]-1-methyl-6-(trifluoromethyl)-2,4(1H,3H)-pyrimidinedione;

3-[2,4-dichloro-5-(2-methyl-2H-tetrazol-5-yl)phenyl]-1-methyl-6-(trifluoromethyl)-2,4(1H,3H)-pyrimidinedione;

3-[4-chloro-3-(2-ethyl-2H-tetrazol-5-yl)phenyl]-1-methyl-6-(trifluoromethyl)-2,4(1H,3H)-pyrimidinedione;

3-[4-chloro-3-(1-methyl-1H-tetrazol-5-yl)phenyl]-1-methyl-6-(trifluoromethyl)-2,4(1H,3H)-pyrimidinedione;

3-[4-chloro-2-fluoro-5-(1-methyl-1H-tetrazol-5-yl)phenyl]-1-methyl-6-(trifluoromethyl)-2,4(1H,3H)-pyrimidinedione;

3-[(2,4-dichloro-5-(1-methyl-1H-tetrazol-5-yl)phenyl]-1-methyl-6-(trifluoromethyl)-2,4(1H,3H)-pyrimidinedione;

3-[(4-chloro-3-(1-ethyl-1H-tetrazol-5-yl)phenyl]-1-methyl-6-(trifluoromethyl)-2,4(1H,3H)-pyrimidinedione;

methyl (5-{2-chloro-5-[1,2,3,6-tetrahydro-3-methyl-2,6-dioxo-4-(trifluoromethyl)pyrimidin-1-yl]phenyl}-1H-tetrazol-1-yl)acetate;

methyl (5-{2-chloro-5-[1,2,3,6-tetrahydro-3-methyl-2,6-dioxo-4-(trifluoromethyl)pyrimidin-1-yl]phenyl}-2H-tetrazol-2-yl)acetate;

methyl (5-{2-chloro-4-fluoro-5-[1,2,3,6-tetrahydro-3-methyl-2,6-dioxo-4-(trifluoromethyl)pyrimidin-1-yl]phenyl}-1H-tetrazol-1-yl)acetate;

methyl (5-{2-chloro-4-fluoro-5-[1,2,3,6-tetrahydro-3-methyl-2,6-dioxo-4-(trifluoromethyl)pyrimidin-1-yl]phenyl}-2H-tetrazol-2-yl)acetate;

methyl (5-{2,4-dichloro-5-[1,2,3,6-tetrahydro-3-methyl-2,6-dioxo-4-(trifluoromethyl)pyrimidin-1-yl]phenyl}-1H-tetrazol-1-yl)acetate;

methyl (5-{2,4-dichloro-5-[1,2,3,6-tetrahydro-3-methyl-2,6-dioxo-4-(trifluoromethyl)pyrimidin-1-yl]phenyl}-2H-tetrazol-2-yl)acetate;

3-[4-chloro-3-(4-methoxy-5-methyl-1,3-thiazol-2-yl)phenyl-6-(trifluoromethyl)-2,4(1H,3H)-pyrimidinedione;

3-[2,4-dichloro-5-(4-methoxy-5-methyl-1,3-thiazol-2-yl)phenyl-6-(trifluoromethyl)-2,4(1H,3H)-pyrimidinedione;

3-[4-chloro-2-fluoro-5-(4-methoxy-5-methyl-1,3-thiazol-2-yl)phenyl-6-(trifluoromethyl)-2,4(1H,3H)-pyrimidinedione;

3-[4-chloro-3-(4-methoxy-5-methyl-1,3-thiazol-2-yl)phenyl-1-methyl-6-(trifluoromethyl)-2,4(1H,3H)-pyrimidinedione;

3-[4-chloro-3-(4-ethoxy-5-methyl-1,3-thiazol-2-yl)phenyl-1-methyl-6-(trifluoromethyl)-2,4(1H,3H)-pyrimidinedione;

3-[(2,4-dichloro-5-(4-methoxy-5-methyl-1,3-thiazol-2-yl)phenyl-1-methyl-6-(trifluoromethyl)-2,4(1H,3H)-pyrimidinedione;

3-[2,4-dichloro-5-(4-ethoxy-5-methyl-1,3-thiazol-2-yl)phenyl-1-methyl-6-(trifluoromethyl)-2,4(1H,3H)-pyrimidinedione;

3-[4-chloro-2-fluoro-5-(4-methoxy-5-methyl-1,3-thiazol-2-yl)phenyl-1-methyl-6-(trifluoromethyl)-2,4(1H,3H)-pyrimidinedione;

3-[4-chloro-2-fluoro-5-(4-ethoxy-5-methyl-1,3-thiazol-2-yl)phenyl-1-methyl-6-(trifluoromethyl)-2,4(1H,3H)-pyrimidinedione;

3-[4-chloro-3-(4-benzyloxy-5-methyl-1,3-thiazol-2-yl)phenyl-1-methyl-6-(trifluoromethyl)-2,4(1H,3H)-pyrimidinedione;

3-[2,4-dichloro-5-(4-benzyloxy-5-methyl-1,3-thiazol-2-yl)phenyl-1-methyl-6-(trifluoromethyl)-2,4(1H,3H)-pyrimidinedione;

3-[4-chloro-2-fluoro-5-(4-benzyloxy-5-methyl-1,3-thiazol-2-yl)phenyl-1-methyl-6-(trifluoromethyl)-2,4(1H,3H)-pyrimidinedione;

3-(2,4-dichloro-5-{[5-(trifluoromethyl)-1,3,4-thiadiazol-2-yl]oxy}phenyl)-6-(trifluoromethyl)-2,4(1H,3H)-pyrimidinedione;

3-(4-chloro-2-fluoro-5-{[5-(trifluoromethyl)-1,3,4-thiadiazol-2-yl]oxy}phenyl)-6-(trifluoromethyl)-2,4(1H,3H)-pyrimidinedione;

3-(2,4-dichloro-5-{[5-(trifluoromethyl)-1,3,4-oxadiazol-2-yl]oxy}phenyl)-6-(trifluoromethyl)-2,4(1H,3H)-pyrimidinedione;

3-(4-chloro-2-fluoro-5-{[5-(trifluoromethyl)-1,3,4-oxadiazol-2-yl]oxy}phenyl)-6-(trifluoromethyl)-2,4(1H,3H)-pyrimidinedione;

3-(4-chloro-3-{[5-(trifluoromethyl)-1,3,4-thiadiazol-2-yl]oxy}phenyl)-1-methyl-6-(trifluoromethyl)-2,4(1H,3H)-pyrimidinedione;

3-(2,4-dichloro-5-{[5-(trifluoromethyl)-1,3,4-thiadiazol-2-yl]oxy}phenyl)-1-methyl-6-(trifluoromethyl)-2,4(1H,3H)-pyrimidinedione;

3-(4-chloro-2-fluoro-5-{[5-(trifluoromethyl)-1,3,4-thiadiazol-2-yl]oxy}phenyl)-1-methyl-6-(trifluoromethyl)-2,4(1H,3H)-pyrimidinedione;

3-{4-chloro-3-[(5-methyl-1,3,4-thiadiazol-2-yl)oxy]phenyl}-1-methyl-6-(trifluoromethyl)-2,4(1H,3H)-pyrimidinedione;

3-{2,4-dichloro-5-[(5-methyl-1,3,4-thiadiazol-2-yl)oxy]phenyl}-1-methyl-6-(trifluoromethyl)-2,4(1H,3H)-pyrimidinedione;

3-{4-chloro-2-fluoro-5-[(5-methyl-1,3,4-thiadiazol-2-yl)oxy]phenyl}-1-methyl-6-(trifluoromethyl)-2,4(1H,3H)-pyrimidinedione;

3-(4-chloro-3-{[5-(trifluoromethyl)-1,3,4-oxadiazol-2-yl]oxy}phenyl)-1-methyl-6-(trifluoromethyl)-2,4(1H,3H)-pyrimidinedione;

3-(2,4-dichloro-5-{[5-(trifluoromethyl)-1,3,4-oxadiazol-2-yl]oxy}phenyl)-1-methyl-6-(trifluoromethyl)-2,4(1H,3H)-pyrimidinedione;

3-(4-chloro-2-fluoro-5-{[5-(trifluoromethyl)-1,3,4-oxadiazol-2-yl]oxy}phenyl)-1-methyl-6-(trifluoromethyl)-2,4(1H,3H)-pyrimidinedione;

3-{4-chloro-3-[(5-methyl-1,3,4-oxadiazol-2-yl)oxy]phenyl}-1-methyl-6-(trifluoromethyl)-2,4(1H,3H)-pyrimidinedione;

3-{2,4-dichloro-5-[(5-methyl-1,3,4-oxadiazol-2-yl)oxy]phenyl}-1-methyl-6-(trifluoromethyl)-2,4(1H,3H)-pyrimidinedione;

3-{4-chloro-2-fluoro-5-[(5-methyl-1,3,4-oxadiazol-2-yl)oxy]phenyl}-1-methyl-6-(trifluoromethyl)-2,4(1H,3H)-pyrimidinedione;

methyl (2E)-4-{2-chloro-4-fluoro-5-[1,2,3,6-tetrahydro-3-methyl-6-oxo-2-thioxo-4-(trifluoromethyl)pyrimidin-1-yl]phenoxy}-3-methoxybut-2-enoate;

methyl (2E)-4-{2-chloro-4-fluoro-5-[1,2,3,6-tetrahydro-3-difluoromethyl-2,6-dioxo-4-(trifluoromethyl)pyrimidin-1-yl]phenoxy}-3-methoxybut-2-enoate.

A further object of the present invention relates to processes for the preparation of the compounds having general formula (I).

In particular, the compounds having general formula (I) can be prepared by the reaction of an isocyanate or isothiocyanate having general formula (II) by cyclocondensation with a 3-aminocrotonate having general formula (III) according to the reaction scheme 1.

Scheme 1:

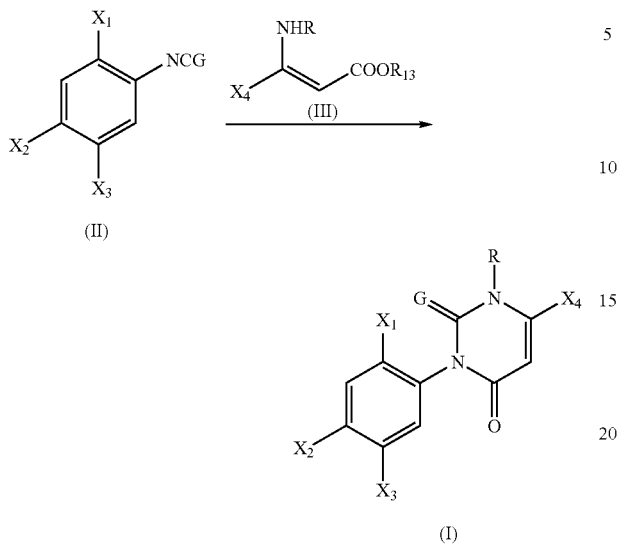

In the general formulae indicated in this reaction scheme:
$X_1$, $X_2$, $X_3$, $X_4$, R and G have the meanings defined above;
$R_{13}$ represents a $C_1$-$C_4$ alkyl or $C_1$-$C_4$ haloalkyl group or a phenyl group possibly substituted with $C_1$-$C_4$ alkyl groups.

The reaction between the compounds having general formula (II) and the compounds having general formula (III) is preferably carried out in the presence of an inert organic solvent and in the presence of an organic base or preferably inorganic, at a temperature ranging from −20° C. to the boiling point of the reaction mixture.

Examples of solvents which can be used for the above reaction include aliphatic or cyclo-aliphatic hydrocarbons (petroleum ether, hexane, cyclohexane, etc.), chlorinated hydrocarbons (methylene chloride, chloroform, carbon tetrachloride, dichloroethane etc.), aromatic hydrocarbons (benzene, toluene, xylene, chlorobenzene, etc.), ethers (diethyl ether, diisopropyl ether, dimethoxy ethane, dioxane, tetrahydrofuran, etc.), alcohols and glycols (methanol, ethanol, methyl cellosolve, ethylene glycol, etc.), ketones (acetone, methyl ethyl ketone, methyl propyl ketone, methyl isobutyl ketone etc.), nitriles (acetonitrile, benzonitrile, etc.), aprotic dipolar solvents (dimethylformamide, dimethylacetamide, hexamethylphosphoramide, dimethylsulfoxide, sulfolane, N-methylpyrrolidone, etc.).

Inorganic bases which can be used are, for example, hydrides, hydroxides and carbonates of sodium and potassium.

Organic bases useful for the purpose are, for example, triethylamine, pyridine, 4-N,N-dimethylaminopyridine, N,N-dimethylaniline, N-methylpiperidine, lutidine, diazabicyclooctane (DABCO), diazabicyclononene (DBN), diazabicycloundecene (DBU).

Isocyanates or isothiocyanates having general formula (II) can be prepared starting from a suitable substituted aniline having general formula (IV) by reaction with a compound having general formula (V), such as phosgene, diphosgene, triphosgene or thiophosgene, according to the reaction scheme 2.

Scheme 2:

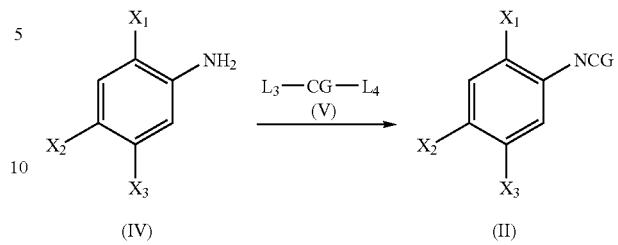

In the general formulae indicated in this reaction scheme:
$X_1$, $X_2$, $X_3$ and G have the meanings defined above;
$L_3$ and $L_4$, the same or different, represent a chlorine atom or a $CCl_3O$— group.

The reaction is preferably carried out in the presence of an inert organic solvent, at a temperature ranging from 0° C. to the boiling point of the mixture, possibly in the presence of a catalyst such as triethylamine, in an amount ranging from 0.001 to 100% by weight with respect to aniline (IV).

Inert organic solvents useful for the purpose are, for example, chlorinated hydrocarbons (for example methylene chloride, chloroform, 1,2-dichloroethane, etc.), aromatic hydrocarbons (for example, benzene, toluene, xylene, chlorobenzene, etc.), esters (for example ethyl acetate, etc.). An amount of reagent (V) ranging from 1 to 3 moles per mole of aniline (IV) is used in the reaction.

The compounds having general formula (I), wherein $X_3$ represents a $Q(CR_1R_2)_nZ$— group, a $Q_1Z$— group, a $Y(OC)$—$CR_6$=$CR_5$—$CR_3R_4Z$— group, compounds (Ia), can also be prepared by the reaction of a uracil having general formula (VI) with a compound having general formula (VII) according to the reaction scheme 3:

Scheme 3:

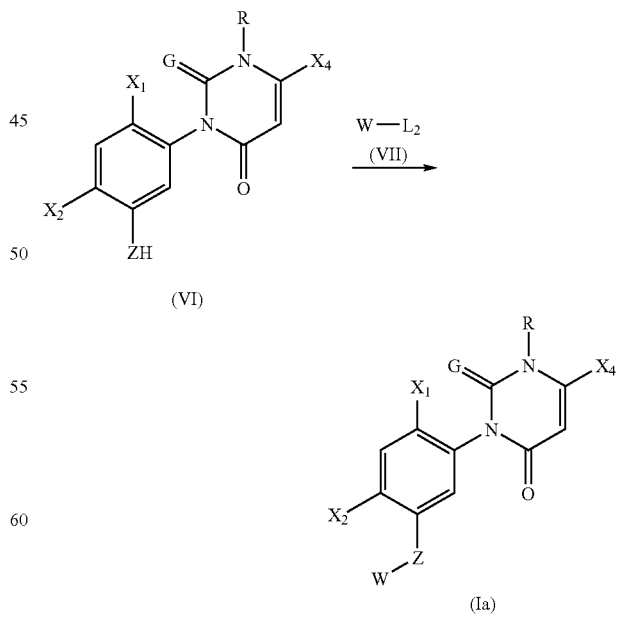

In the general formulae indicated in this reaction scheme:
$X_1$, $X_2$, $X_4$, G and Z have the meanings defined above;

R represents a $C_1$-$C_3$ alkyl group or a $C_1$-$C_3$ haloalkyl group;

W represents a $Q(CR_1R_2)_n$— group, a $Q_1$- group, a Y(OC)—$CR_6$=$CR_5$—$CR_3R_4$— group, wherein $R_1$, $R_2$, $R_3$, $R_4$, $R_5$, $R_6$, Y, Q and $Q_1$ have the meanings defined above;

$L_2$ represents a halogen atom, a $R_LSO_2O$— group, wherein $R_L$ represents a $C_1$-$C_4$ alkyl or $C_1$-$C_4$ haloalkyl group or a phenyl group possibly substituted by $C_1$-$C_4$ alkyl groups, or it represents a $R_{L1}SO_2$— group wherein $R_{L1}$ represents a $C_1$-$C_4$ alkyl or $C_1$-$C_4$ haloalkyl group.

The reaction between the compounds having general formula (VI) and the compounds having general formula (VII) is preferably carried out in the presence of one or more inert organic solvents and in the presence of a base, preferably an inorganic base, at a temperature ranging from −10° C. to the boiling temperature of the reaction mixture.

Organic solvents useful for the purpose are, for example, aromatic hydrocarbons (benzene, toluene, xylene, chlorobenzene, etc.), ethers (diethyl ether, diisopropyl ether, dimethoxyethane, dioxane, tetrahydrofuran, etc.), alcohols and glycols (methanol, ethanol, methyl cellosolve, ethylene glycol, etc.), ketones (acetone, methyl ethyl ketone, methyl propyl ketone, methyl isobutyl ketone, etc.), nitrites (acetonitrile, benzonitrile, etc.), aprotic dipolar solvents (dimethylformamide, dimethylacetamide, hexamethylphosphoramide, dimethylsulfoxide, sulfolane, N-methylpyrrolidone, etc.).

Inorganic bases useful for the purpose are, for example, hydrides, hydroxides and carbonates of sodium or potassium.

The reaction can also be advantageously carried out in a biphasic system using, as the solvent, water and an organic solvent immiscible with water, in the presence of phase transfer catalysts, according to what is described by Dehmlow and Dehmlow in "Phase Transfer Catalysis" (1983), Verlag Chemie.

The compounds having general formula (I) wherein G=O and R≠H, compounds (Ic), can also be prepared by the reaction of a uracil having general formula (Ib) with an alkylation compound having general formula (VIII) according to the reaction scheme 4.

Scheme 4:

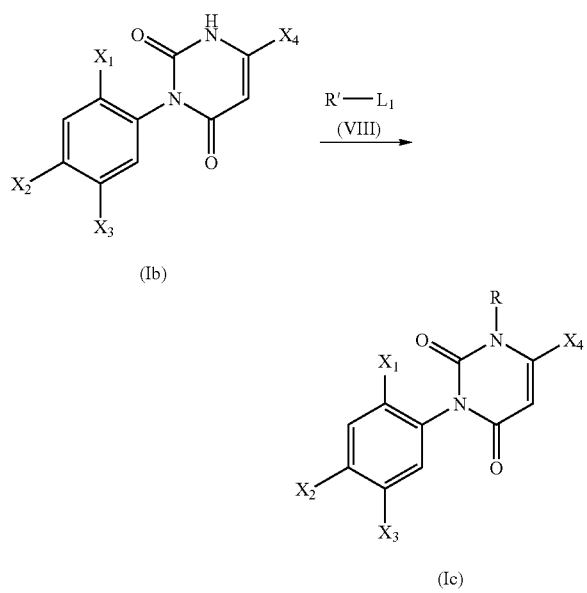

In the general formulae indicated in this reaction scheme:
$X_1$, $X_2$, $X_3$ and $X_4$ have the meanings defined above;
R' represents a $C_1$-$C_3$ alkyl or $C_1$-$C_3$ haloalkyl group;
$L_1$ represents a halogen atom, or a $R_LSO_2O$— group wherein $R_L$ represents a $C_1$-$C_4$ alkyl or $C_1$-$C_4$ haloalkyl group or a phenyl group possibly substituted by $C_1$-$C_4$ alkyl groups.

The reaction between the compounds having general formula (Ib) and the compounds having general formula (VIII) is preferably carried out in the presence of one or more inert organic solvents and in the presence of a base, preferably an inorganic base, at a temperature ranging from −10° C. to the boiling temperature of the reaction mixture.

Organic solvents useful for the purpose are, for example, aromatic hydrocarbons (benzene, toluene, xylene, chlorobenzene, etc.), ethers (diethyl ether, diisopropyl ether, dimethoxyethane, dioxane, tetrahydrofuran, etc.), alcohols and glycols (methanol, ethanol, methyl cellosolve, ethylene glycol, etc.), ketones (acetone, methyl ethyl ketone, methyl propyl ketone, methyl isobutyl ketone, etc.), nitriles (acetonitrile, benzonitrile, etc.), aprotic dipolar solvents (dimethylformamide, dimethylacetamide hexamethylphosphoramide, dimethylsulfoxide, sulfolane, N-methylpyrrolidone, etc.).

Inorganic bases useful for the purpose are, for example, hydrides, hydroxides and carbonates of sodium and potassium.

The reaction can also be advantageously carried out in a biphasic system using, as solvent, water and an organic solvent immiscible with water, in the presence of phase transfer catalysts, according to what is described by Dehmlow and Dehmlow in "Phase Transfer Catalysis" (1983), Verlag Chemie.

The compounds having general formula (I) wherein G=O, compounds (Id), can also be prepared starting from a suitably substituted aniline having formula (IV) by reaction with a chloroformiate or a carbonate having formula (IX) to give a carbamate having formula (X); this can be converted to the compounds of general formula (Id) by cyclo condensation with a 3-aminocrotonate having general formula (III).

This reaction sequence is shown in scheme 5.

Scheme 5:

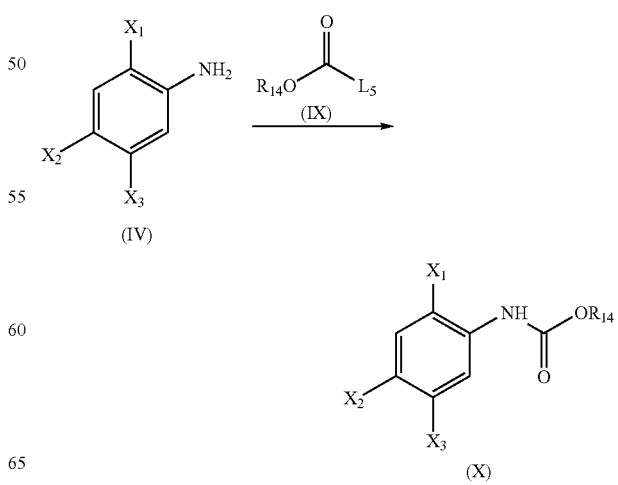

-continued

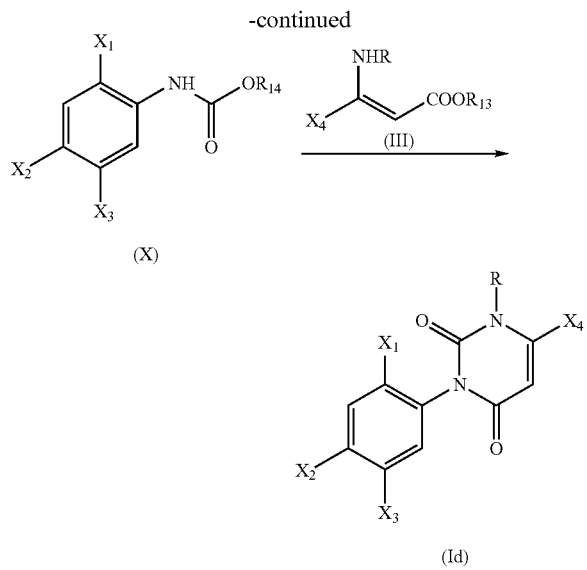

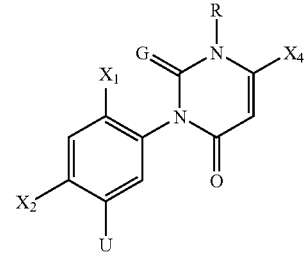

In the general formulae shown in the reaction scheme:

$X_1$, $X_2$, $X_3$, $X_4$ and R have the meanings defined above;
$L_5$ represents a halogen atom or a $OR_{14}$ group;
$R_{13}$ and $R_{14}$ represent a $C_1$-$C_4$ alkyl or $C_1$-$C_4$ haloalkyl group or a phenyl group possibly substituted by $C_1$-$C_4$ alkyl groups.

The reaction between aniline having general formula (IV) and a compound having general formula (IX) is preferably carried out in the presence of an inert organic solvent, at a temperature ranging from −10° C. to the boiling point of the mixture itself, in the presence of an organic or inorganic base, in an amount ranging from 1 to 1.5 moles per mole of aniline (IV).

Inorganic bases useful for the purpose are, for example, sodium carbonate, sodium hydroxide, etc.

Organic bases useful for the purpose are, for example, triethylamine, pyridine, 4-dimethylaminopyridine, etc.

Inert organic solvents useful for the purpose are, for example, chlorinated hydrocarbons (for example, methylene chloride, chloroform, 1,2-dichloroethane etc.), aromatic hydrocarbons (for example benzene, toluene, xylene, chlorobenzene, etc.), ethers (for example, ethyl ether, tetrahydrofuran, dioxane, etc.), esters (for example ethyl acetate, etc.).

A quantity of the compound having formula (IX) ranging from 1 to 1.5 moles per mole of aniline (IV), is used in the reaction.

The operative conditions, as well as the typology of solvent and bases useful for carrying out the cyclocondensation reaction of a carbamate having general formula (X) with a 3-aminocrotonate having general formula (III) shown in scheme 5, are analogous to those shown for the reaction of scheme 1.

The compounds having general formula (I) wherein $X_3=Q_2$ can also be prepared starting from compounds having general formula (XI)

wherein:
$X_1$, $X_2$, $X_4$, R and G have the meanings defined above;
U represents a functional group which can be transformed into one of the heterocyclic rings envisaged for $Q_2$.

For example, when U=CN, $CONH_2$, $CSNH_2$, $CO_2H$ ecc., said functional groups can be easily transformed into heterocyclic groups according to known techniques in organic chemistry.

Specific examples of this strategy, for example starting from the cyano functional group (U=CN), relate to the preparation of tetrazoles and thiazoles.

The cyano group can be transformed into a tetrazole, for example by reaction under heat with trimethyl silylazide, in toluene, catalysed by dibutyltin oxide, according to what is described in "Journal Organic Chemistry" (1993), vol. 58, pages 4139-4141, or by heating with sodium azide in water and catalysis of $ZnBr_2$, as described in "Journal Organic Chemistry" (2001), vol. 66, pages 7945-7950.

The cyano group can be transformed into thiazole, for example by reaction under heat with α-mercapto acetic acids according to what is described in "Journal Medicinal Chemistry" (1991), vol. 34, pages 2158-2165, or by treatment with α-mercapto ketones and gaseous hydrochloric acid, in benzene, at 0° C., as described in C.A., 1958, vol. 52, 14698.

The compounds having general formula (Ib) can also be prepared starting from a suitable substituted aniline having general formula (IV) by reaction with a β-ketoester having general formula (XII), to give an anilide having general formula (XIII); this can be easily converted into the intermediate of general formula (XIV) by amination with ammonia or ammonium salts; this last intermediate can be converted into the compounds of general formula (Ib) by cyclization with a compound of general formula (XV), such as phosgene, or diphosgene.

This reaction sequence is shown in scheme 6.

Scheme 6:

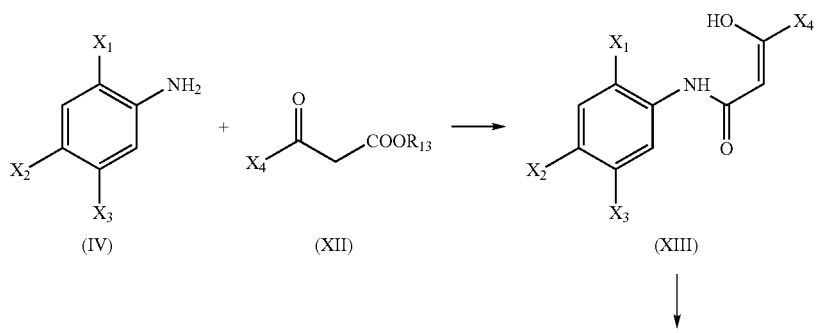

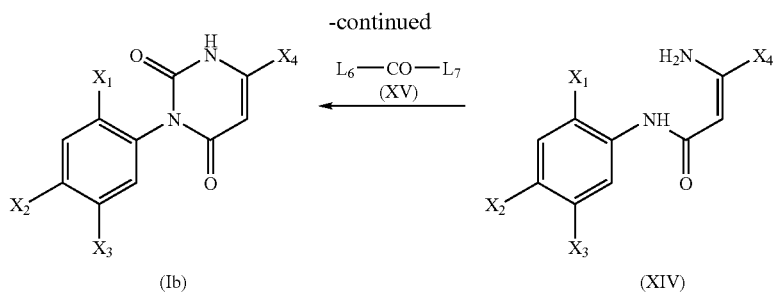

(Ib)            (XIV)

In the general formulae indicated in this reaction scheme:

$X_1$, $X_2$, $X_3$ and $X_4$ have the meanings defined above;

$R_{13}$ represents a $C_1$-$C_4$ alkyl or haloalkyl group or a phenyl group possibly substituted by $C_1$-$C_4$ alkyl groups;

$L_6$ and $L_7$, having the same or different meaning, represent a chlorine atom, a $CCl_3O$— group, a $C_1$-$C_4$ alkoxy group, a phenoxy group, an imidazol-1-yl group or a 1,2,4-triazol-1-yl group.

The reaction between the compounds having general formula (IV) and the compounds having general formula (XII) is preferably carried out in the presence of one or more inert organic solvents, at a temperature ranging from −10° C. to the boiling temperature of the reaction mixture; an amount of compound (XII) ranging from 1 to 3 moles per mole of aniline (IV) is used in the reaction.

The reaction may also be carried out while distilling off compound $R_{13}OH$ formed during the reaction, alone or in mixture with the solvent used.

Inert organic solvents useful for the purpose are, for example, aliphatic or cyclo-aliphatic hydrocarbons (petroleum ether, hexane, cyclohexane, etc.), chlorinated hydrocarbons (for example methylene chloride, chloroform, 1,2-dichloroethane, etc.), aromatic hydrocarbons (for example, benzene, toluene, xylene, chlorobenzene, etc.), ethers (for example diethyl ether, tetrahydrofuran, dioxane, etc.), nitriles (acetonitrile, benzonitrile, etc.), aprotic dipolar solvents (dimethylformamide, dimethylacetamide, hexamethylphosphoramide, dimethylsulfoxide, sulfolane, N-methylpyrrolidone, etc.).

The reaction may also be carried out in presence of a suitable organic base, for example pyridine, 4-dimethylaminopyridine, etc., in an amount ranging from 0.001 to 1 mole per mole of compound (IV).

The transformation of compounds having general formula (XIII) into compounds having general formula (XIV) is preferably carried out in the presence of one or more inert organic solvents, at a temperature ranging from −10° C. to the boiling temperature of the reaction mixture; in the reaction ammonia or a suitable ammonium salt, for example ammonium acetate, is used in an amount ranging from 1 to 20 moles per mole of compound (XIII).

Inert organic solvents useful for the purpose are, for example, chlorinated hydrocarbons (for example methylene chloride, chloroform, 1,2-dichloroethane, etc.), aromatic hydrocarbons (for example, benzene, toluene, xylene, chlorobenzene, etc.), ethers (for example diethyl ether, tetrahydrofuran, dioxane, etc.), nitriles (acetonitrile, benzonitrile, etc.), aprotic dipolar solvents (dimethylformamide, dimethylacetamide, hexamethylphosphoramide, dimethylsulfoxide, sulfolane, N-methylpyr-methylpyrrolidone, etc.).

Alternatively, when an ammonium salt is used, the reaction may be carried out in absence of solvent, at a temperature ranging from 20° C. to 200° C.

The reaction between the compounds having general formula (XIV) and the compounds having general formula (XV) is preferably carried out in the presence of one or more inert organic solvents, at a temperature ranging from −10° C. to the boiling temperature of the reaction mixture; an amount of compound (XV) ranging from 1 to 5 moles per mole of compound (XIV) is used in the reaction.

The reaction is preferably carried out in the presence of a suitable organic or inorganic base, in an amount ranging from 1 to 5 moles per mole of compound (XIV).

Inorganic bases useful for the purpose are, for example, hydroxides and carbonates of sodium and potassium, etc.

Organic bases useful for the purpose are, for example, triethylamine, pyridine, 4-dimethylaminopyridine, etc.

In addition to the base a suitable catalyst is preferably used, for example 4-dimethylaminopyridine, in an amount ranging from 0.001 to 1 mole per mole of compound (XIV).

Inert organic solvents useful for the purpose are, for example, esters (for example ethyl acetate, etc.), chlorinated hydrocarbons (for example methylene chloride, chloroform, 1,2-dichloroethane, etc.), aromatic hydrocarbons (for example, benzene, toluene, xylene, chlorobenzene, etc.), alcohols and glycols (methanol, ethanol, methyl cellosolve, ethylene glycol, etc.), ketones (acetone, methyl ethyl ketone, methyl propyl ketone, methyl isobutyl ketone, etc.), ethers (for example diethyl ether, tetrahydrofuran, dioxane, etc.), nitriles (acetonitrile, benzonitrile, etc.), aprotic dipolar solvents (dimethylformamide, dimethylacetamide, hexamethylphosphoramide, dimethylsulfoxide, sulfolane, N-methylpyrrolidone, etc.).

The intermediate products having general formulae (III), (V), (VII), (VIII), (IX), (XII) and (XV) when not known per se, are easily prepared according to known methods of organic chemistry.

In some cases, the compounds having general formula (I), can be obtained as two or more optical or geometric or position isomers.

It is therefore within the spirit of the present invention to consider both the isomerically pure compounds having general formula (I), and mixtures of the same, optionally obtained during the preparation of the compounds having general formula (I) or deriving from an incomplete separation of the isomers, in any proportion.

As already mentioned, the compounds having general formula (I) have a high herbicidal activity which makes them suitable for use in the agricultural field for the defence of useful crops from weeds.

In particular the compounds object of the present invention are effective in the control, in both preemergence and postemergence, of numerous monocotyledonous and dicotyledonous weeds. At the same time these compounds can show compatibility or absence of toxic effects with respect to useful crops in pre- and/or post-emergence treatment.

The compounds of the present invention can act as total or selective herbicides also in relation to the amount of the active principle used.

Examples of weeds which can be efficaciously controlled by using the compounds having general formula (I), are: *Abutilon theofrasti, Alisma plantago, Amaranthus* spp., *Amni maius, Capsella bursa pastoris, Chenopodium album, Convolvulus sepium, Galium aparine, Geranium dissectum, Ipomea* spp., *Matricaria* spp., *Papaver rhoaes, Phaseolus aureus, Polygonum persicaria, Portulaca oleracea, Sida spinosa, Sinapsis arvensis, Solanum nigrum, Stellaria media, Veronica* spp., *Viola* spp., *Xanthium* spp., *Alopecurus myosuroides, Avena fatua, Cyperus* spp., *Digitaria sanguinalis, Echinocloa* spp., *Heleocaris avicularis, Heteranthera* spp., *Panicum* spp., *Poa* spp., *Scirpus* spp., *Sorghum* spp., etc.

Many of the above compounds do not have toxic effects, at the dosage of use in agrarian applications, against one or more important crops, such as rice (*Oryza sativa*), wheat (*Triticum* sp.), barley (*Hordeum vulgare*), corn (*Zea mays*), soya-bean (*Glycine max*).

A further object of the present invention relates to a method for the control of weeds in cultivated areas by the application of the compounds having general formula (I).

The quantity of compound to be used for obtaining the desired effect can vary in relation to several factors, such as, for example, the compound used, the crop to be preserved, the weed to be fought, the degree of infestation, the climatic conditions, the characteristics of the soil, the application method, etc.

Dosages of compound ranging from 1 g to 1000 g per hectare generally provide a sufficient control.

For use in agriculture, it is often advantageous to use compositions with a herbicidal activity, containing, as active substance, one or more compounds having general formula (I), possibly also as a mixture of isomers.

Compositions can be used in the form of dry powders, wet powders, emulsifiable concentrated products, microemulsions, pastes, granulates, solutions, suspensions, etc.: the selection of the type of composition depends on the specific use.

The compositions are prepared according to known methods, for example by diluting or dissolving the active ingredient with a solvent medium and/or solid diluent, possibly in the presence of surface-active agents.

Kaolin, alumina, silica, talc, bentonite, chalk, quartz, dolomite, attapulgite, montmorillonite, diatom earth, cellulose, starch, etc, can be used as inert solid diluents, or carriers.

Water, or organic solvents such as aromatic hydrocarbons (xylols, mixtures or alkyl benzenes, etc.), aliphatic hydrocarbons (hexane, cyclohexane, etc.), halogenated aromatic hydrocarbons (chlorobenzene, etc.), alcohols (methanol, propanol, butanol, octanol, etc.), esters (isobutyl acetate, etc.), ketones (acetone, cyclohexanone, acetophenone, isophorone, ethyl amyl ketone, etc.), or vegetal or mineral oils or mixture thereof, etc. can be used as inert liquid diluents.

Surface-active agents which can be used are wetting and emulsifying agents of the non-ionic type (polyethoxylated alkyl phenols, polyethoxylated fatty alcohols, etc.), of the anionic type (alkyl benzene sulfonates, alkyl sulfonates, etc.), of the cationic type (quaternary salts of alkyl ammonium, etc.).

Dispersants can also be added (for example lignin and its salts, cellulose derivatives, alginates, etc.), stabilizers (for example antioxidants, UV absorbers, etc.).

In order to widen the range of activity of the above compositions, it is possible to add other active ingredients, such as, for example, other herbicides, fungicides, insecticides, acaricides, fertilizers, etc.

Examples of other herbicides which can be added to the compositions containing one or more compounds having general formula (I) are the following:

acetochlor, acifluorfen, aclonifen, AKH-7088, alachlor, alloxydim, ametryn, amicarbazone, amidosulfuron, amitrole, anilofos, asulam, atrazine, azafenidin, azimsulfuron, aziprotryne, BAY MKH 6561, beflubutamid, benazolin, benfluralin, benfuresate, bensulfuron, bensulide, bentazone, benzfendizone, benzobicyclon, benzofenap, benzthiazuron, bifenox, bilanafos, bispyribac-sodium, bromacil, bromobutide, bromofenoxim, bromoxynil, butachlor, butafenacil, butamifos, butenachlor, butralin, butroxydim, butylate, cafenstrole, carbetamide, carfentrazone-ethyl, chlomethoxyfen, chloramben, chlorbromuron, chlorbufam, chlorflurenol, chloridazon, chlorimuron, chlornitrofen, chlorotoluron, chloroxuron, chlorpropham, chlorsulfuron, chlorthal, chlorthiamid, cinidon ethyl, cinmethylin, cinosulfuron, clethodim, clodinafop, clomazone, clomeprop, clopyralid, cloransulam-methyl, cumyluron (JC-940), cyanazine, cycloate, cyclosulfamuron, cycloxydim, cyhalofop-butyl, 2,4-D, 2,4-DB, daimuron, dalapon, desmedipham, desmetryn, dicamba, dichlobenil, dichlorprop, dichlorprop-P, diclofop, diclosulam, diethatyl, difenoxuron, difenzoquat, diflufenican, diflufenzopyr, dimefuron, dimepiperate, dimethachlor, dimethametryn, dimethenamid, dinitramine, dinoseb, dinoseb acetate, dinoterb, diphenamid, dipropetryn, diquat, dithiopyr, 1-diuron, eglinazine, endothal, EPTC, esprocarb, ethalfluralin, ethametsulfuron-methyl, ethidimuron, ethiozin (SMY 1500), ethofumesate, ethoxyfen-ethyl (HC-252), ethoxysulfuron, etobenzanid (HW 52), fenoxaprop, fenoxaprop-P, fentrazamide, fenuron, flamprop, flamprop-M, flazasulfuron, florasulam, fluazifop, fluazifop-P, fluazolate (JV 485), flucarbazone-sodium, fluchloralin, flufenacet, flufenpyr ethyl, flumetsulam, flumiclorac-pentyl, flumioxazin, flumipropin, fluometuron, fluoroglycofen, fluoronitrofen, flupoxam, flupropanate, flupyrsulfuron, flurenol, fluridone, flurochloridone, fluroxypyr, flurtamone, fluthiacet-methyl, fomesafen, foramsulfuron, fosamine, furyloxyfen, glufosinate, glyphosate, halosulfuron-methyl, haloxyfop, haloxyfop-P-methyl, hexazinone, imazamethabenz, imazamox, imazapic, imazapyr, imazaquin, imazethapyr, imazosulfuron, indanofan, iodosulfuron, ioxynil, isopropalin, isoproturon, isouron, isoxaben, isoxachlortole, isoxaflutole, isoxapyrifop, KPP-421, lactofen, lenacil, linuron, LS830556, MCPA, MCPA-thioethyl, MCPB, mecoprop, mecoprop-P, mefenacet, mesosulfuron, mesotrione, metamitron, metazachlor, methabenzthiazuron, methazole, methoprotryne, methyldymron, metobenzuron, metobromuron, metolachlor, S-metolachlor, metosulam, metoxuron, metribuzin, metsulfuron, molinate, monalide, monolinuron, naproanilide, napropamide, naptalam, NC-330, neburon, nicosulfuron, nipyraclofen, norflurazon, orbencarb, oryzalin, oxadiargyl, oxadiazon, oxasulfuron, oxaziclomefone, oxyfluorfen, paraquat, pebulate, pendimethalin, penoxsulam, pentanochlor, pentoxazone, pethoxamid, phenmedipham, picloram, picolinafen, piperophos, prethylachlor, primisulfuron, prodiamine, profluazol, proglinazine, prometon, prometryne, propachlor, propanil, propaquizafop, propazine, propham, propisochlor, propyzamide, prosulfocarb, prosulfuron, pyraclonil, pyraflufenethyl, pyrazogyl (HSA-961), pyrazolynate, pyrazosulfuron, pyrazoxyfen, pyribenzoxim, pyributicarb, pyridafol, pyridate, pyriftalid, pyriminobac-methyl, pyrithiobac-sodium, quinclorac, quinmerac, quizalofop, quizalofop-P, rimsulfuron, sethoxydim, siduron, simazine, simetryn, sulcotrione, sulfentrazone, sulfometuron-methyl, sulfosulfuron, 2,3,6-TBA, TCA-sodium, tebutam, tebuthiuron, tepraloxydim, terbacil, terbumeton, terbuthylazine, terbutryn, thenylchlor, thiazafluron, thiazopyr, thidiazimin, thifensulfuron-methyl, thiobencarb, tiocarbazil, tioclorim, tralkoxydim, tri-allate, triasulfuron, triaziflam, tribenuron, triclopyr, trietazine, trifloxysulfuron, trifluralin, triflusulfuron-methyl, tritosulfuron, UBI-C4874, vernolate.

The concentration of active substance in the above compositions can vary within a wide range, depending on the active substance, the applications to which it is destined, the environmental conditions and type of formulation used. In general, the concentration of active substance preferably ranges from 1 to 90%.

Some illustrative and non-limiting examples of the present invention are provided hereunder.

Example 1

Preparation of methyl (2E)-4-(2-chloro-4-fluoro-5-isocyanatophenoxy)-3-methoxybut-2-enoate (Intermediate having formula II)

Trichloromethyl chloroformate (1.37 g) is added dropwise to a solution of methyl (2E)-4-(5-amino-2-chloro-4-fluorophenoxy)-3-methoxybut-2-enoate (2.0 g) in ethyl acetate (30 ml). The mixture is stirred overnight at room temperature. It is concentrated under vacuum and the residue obtained (2.3 g) is used as such in the subsequent reaction.

Example 2

Preparation of methyl (2E)-4-{2-chloro-4-fluoro-5-[1,2,3,6-tetrahydro-2,6-dioxo-4-(trifluoromethyl)pyrimidin-1-yl]phenoxy}-3-methoxybut-2-enoate (Compound No 1)

A solution of ethyl 3-amino-4,4,4-trifluoro-2-butenoate (1.39 g) in dimethylformamide (5 ml) is added drop-wise to a suspension of sodium hydride (60% in mineral oil) (0.3 g) in dimethylformamide (15 ml), cooled to 0° C. and kept in an inert atmosphere, the temperature being maintained below 5° C. At the end of the addition, the mixture is stirred for 1 hour at a temperature ranging from 2 to 4° C. A solution of methyl (2E)-4-(2-chloro-4-fluoro-5-isocyanatophenoxy)-3-methoxybut-2-enoate (2.3 g), prepared in the previous example 1, in dimethylformamide (7 ml) is added dropwise to the solution thus obtained, maintaining the temperature within the above-mentioned range.

The reaction mixture is subsequently heated to 80° C., maintained at this temperature for 4.5 hours and finally stirred overnight at room temperature. The reaction mixture is poured into water (100 ml) and washed with ethyl acetate (3×30 ml). The organic phase is extracted with water that is added to the previous aqueous phase and acidified with 10% hydrochloric acid at a temperature of 5° C. The product which separates is extracted with ethyl acetate and dried under vacuum. 2.74 g of product are obtained, which are used as such in the following reaction.

$^1$H-NMR (CDCl$_3$): δ a 3.67, 3.69 (2s, 6H, CO$_2$CH$_3$, OCH$_3$); 5.20 (bs, 1H, CHCO$_2$Me); 5.25 (m, 2H, OCH$_2$); 6.23 (s, 1H, CH uracil); 6.9 (d, 1H, aromatic); 7.3 (d, 1H, aromatic).

Example 3

Preparation of methyl (2E)-4-{2-chloro-4-fluoro-5-[1,2,3,6-tetrahydro-3-methyl-2,6-dioxo-4-(trifluoromethyl)pyrimidin-1-yl]phenoxy}-3-methoxybut-2-enoate (Compound No 2)

Methyl iodide (0.4 g) is added to a mixture of methyl (2E)-4-{2-chloro-4-fluoro-5-[1,2,3,6-tetrahydro-2,6-dioxo-4-(trifluoromethyl)pyrimidin-1-yl]phenoxy}-3-methoxybut-2-enoate (0.89 g), obtained in the previous example 2, and potassium carbonate (0.4 g) in acetone (15 ml). The reaction mixture is refluxed for 5 hours. Water is added (100 ml) after evaporation of the solvent, and the mixture is extracted ethyl acetate (2×50 ml); the organic phase is dried with sodium sulphate and concentrated under vacuum. The residue is purified by chromatography on a silica gel column, eluting with n-hexane/ethyl acetate 6:4. 0.5 g of product are obtained.

$^1$H-NMR (CDCl$_3$): δ a 3.53 (bs, 1H, NCH$_3$); 3.66, 3.67 (2s, 6H, CO$_2$CH$_3$, OCH$_3$); 5.18 (bs, 1H, CHCO$_2$Me); 5.23 (m, 2H, OCH$_2$); 6.33 (s, 1H, CH uracil); 6.9 (d, 1H, aromatic); 7.3 (d, 1H, aromatic).

Example 4

Alternative preparation of methyl (2E)-4-{2-chloro-4-fluoro-5-[1,2,3,6-tetrahydro-3-methyl-2,6-dioxo-4-(trifluoromethyl)pyrimidin-1-yl]phenoxy}-3-methoxybut-2-enoate (Compound No 2)

A solution of ethyl 4,4,4-trifluoro-3-(methylamino)-2-butenoate (3.25 g) in dimethylformamide (10 ml) is added drop-wise to a suspension of sodium hydride (60% in mineral oil) (0.65 g) in dimethylformamide (35 ml), cooled to 0° C. and kept in an inert atmosphere, maintaining the temperature below 5° C. At the end of the addition, the solution is stirred for an hour at a temperature ranging from 2 to 4° C. A solution of methyl (2E)-4-(2-chloro-4-fluoro-5-isocyanatophenoxy)-3-methoxybut-2-enoate (5.0 g) in dimethyl formamide (10 ml) is added drop-wise to the solution thus obtained, maintaining the temperature within the above-mentioned range.

The reaction mixture is then heated to 100° C., maintained at this temperature for 6 hours and finally stirred overnight at room temperature. The reaction mixture is poured into water (200 ml) and washed with ethyl acetate (3×50 ml). The organic phase is extracted with water that is added to the previous aqueous phase and acidified with 10% hydrochloric acid at a temperature of 5° C. The product which separates is extracted with ethyl acetate and dried under vacuum. The residue is purified by chromatography on a silica gel column, eluting with n-hexane/ethyl acetate 6:4. 2.1 g of product are obtained.

Example 5

The following compounds were prepared (identified by elemental analysis, $^1$H- and $^{19}$F-NMR), following the procedures described in the above examples:

methyl (2E)-4-{2,4-dichloro-5-[1,2,3,6-tetrahydro-3-methyl-2,6-dioxo-4-(trifluoromethyl)pyrimidin-1-yl]phenoxy}-3-methoxybut-2-enoate (Compound No 3), m.p. 116° C.;

ethyl (2E)-4-{2-chloro-4-fluoro-5-[1,2,3,6-tetrahydro-3-methyl-2,6-dioxo-4-(trifluoromethyl)pyrimidin-1-yl]phenoxy}-3-ethoxybut-2-enoate (Compound No 4);

ethyl (2E)-4-{2,4-dichloro-5-[1,2,3,6-tetrahydro-3-methyl-2,6-dioxo-4-(trifluoromethyl)pyrimidin-1-yl]phenoxy}-3-ethoxybut-2-enoate (Compound No 5);

Example 6

Preparation of 3-{5-[(5-tert-butyl-1,3,4-oxadiazol-2-yl) methoxy]-4-chloro-2-fluorophenyl}-1-methyl-6-(trifluoromethyl)-2,4(1H,3H)-pyrimidinedione (Compound No 6)

2-tert-butyl-5-(chloromethyl)-1,3,4-oxadiazole (0.22 g) is added to a mixture of 3-(4-chloro-2-fluoro-5-hydroxyphenyl)-1-methyl-6-(trifluoromethyl)-2,4(1H,3H)-pyrimidinedione (0.40 g) and potassium carbonate (0.25 g) in dimethylformamide (5 ml). The reaction mixture is heated to 60° C. for 5 hours.

At the end of the reaction, the mixture is poured into water (50 ml) and extracted with ethyl acetate (2×30 ml); the organic phase is washed with water, dried with sodium sulphate and concentrated under vacuum. The residue is purified by chromatography on a silica gel column, eluting with n-hexane/ethyl acetate 8:2. 0.24 g of product are obtained as a colourless oil.

$^1$H-NMR (CDCl$_3$): δ a 1.41 (s, 9H, C(CH$_3$)$_3$); 3.53 (bs, 3H, NCH$_3$); 5.25 (s, 2H, OCH$_2$); 6.33 (s, 1H, CH uracil); 7.1 (d, 1H, aromatic); 7.3 (d, 1H, aromatic).

Example 7

The following compounds (identified by elemental analysis, $^1$H- and $^{19}$F-NMR) were prepared following the procedure described in example 6:

3-[4-chloro-2-fluoro-5-(tetrazol-5-ylmethoxy)phenyl]-1-methyl-6-(trifluoromethyl)-2,4(1H,3H)-pyrimidinedione (Compound No 7) m.p. 82° C.;

3-{4-chloro-2-fluoro-5-[(2-ethyl-2H-tetrazol-5-yl)methoxy]phenyl}-1-methyl-6-(trifluoromethyl)-2,4(1H,3H)-pyrimidinedione (Compound No 8) m.p. 126° C.;

3-{4-chloro-2-fluoro-5-[(1-ethyl-1H-tetrazol-5-yl)methoxy]phenyl}-1-methyl-6-(trifluoromethyl)-2,4(1H,3H)-pyrimidinedione (Compound No 9) m.p. 60° C.;

methyl [5-({2-chloro-4-fluoro-5-[1,2,3,6-tetrahydro-3-methyl-2,6-dioxo-4-(trifluoromethyl)pyrimidin-1-yl]phenoxy}methyl)-1H-tetrazol-1-yl]acetate (Compound No 10) m.p. 243° C.;

methyl [5-({2-chloro-4-fluoro-5-[1,2,3,6-tetrahydro-3-methyl-2,6-dioxo-4-(trifluoromethyl)pyrimidin-1-yl]phenoxy}methyl)-2H-tetrazol-2-yl]acetate (Compound No 11) m.p. 65° C.;

Example 8

Preparation of ethyl 4-chloro-3-cyanophenylcarbamate (Intermediate having formula X)

A solution of ethyl chloroformate (3.68 g) in methylene chloride (5 ml) is added dropwise in about 20 minutes to a mixture of 5-amino-2-chlorobenzonitrile (5.2 g) and pyridine (2.77 g) in methylene chloride (75 ml), cooled to 0° C. and maintained in an inert atmosphere. At the end of the addition, the solution is stirred for 1 hour at 0° C. and is then brought to room temperature. At the end of the reaction, the mixture is poured into water (100 ml) and extracted with methylene chloride (2×80 ml); the organic phase is washed with water (2×80 ml), dried with sodium sulphate and concentrated under vacuum. 7.2 g of product are obtained.

$^1$H-NMR (CDCl$_3$): δ a 1.31 (t, 3H, CH$_3$); 4.24 (q, 2H, CH$_2$); 6.72 (bs, 1H, NH); 7.25-7.82 (m, 3H, aromatic).

Example 9

Preparation of 2-chloro-5-[1,2,3,6-tetrahydro-2,6-dioxo-4-(trifluoromethyl)pyrimidin-1-yl]benzonitrile A solution of ethyl 3-amino-4,4,4-trifluoro-2-butenoate (3.48 g) in dimethylformamide (7 ml) is added dropwise to a suspension of sodium hydride (60% in mineral oil) (0.9 g) in dimethylformamide (20 ml), cooled to 0° C. and kept in an inert atmosphere, maintaining the temperature below 5° C. At the end of the addition, the solution is stirred for 1 hour at a temperature between 0 and 5° C. A solution of ethyl 4-chloro-3-cyanophenylcarbamate (4.0 g), prepared in the previous example 8, in dimethylformamide (30 ml) is added dropwise to the solution thus obtained, the temperature being maintained within the above-mentioned range.

The reaction mixture is then heated to 140° C. and maintained at this temperature for 4.5 hours. It is subsequently poured into water (100 ml), basified with 10% NaOH and extracted with ethyl ether (3×50 ml). The aqueous phase is acidified with 10% hydrochloric acid. The product which separates is extracted with ethyl acetate (2×80 ml) dried with sodium sulphate and concentrated under vacuum. 6.1 g of product are obtained, which is used as such in the subsequent reaction.

Example 10

Preparation of 2-chloro-5-[1,2,3,6-tetrahydro-3-methyl-2,6-dioxo-4-(trifluoromethyl)pyrimidin-1-yl]benzonitrile Methyl iodide (10.8 g) is added to a mixture of 2-chloro-5-[1,2,3,6-tetrahydro-2,6-dioxo-4-(trifluoromethyl)pyrimidin-1-yl]benzonitrile (6.0 g), obtained in the previous example 9, and sodium bicarbonate (3.19 g) in acetone (70 ml). The reaction mixture is refluxed for 18 hours. Water is added (200 ml) after the evaporation of the solvent, and the mixture is extracted with ethyl acetate (3×100 ml), the organic phase is dried with sodium sulphate and concentrated under vacuum. The residue is purified by chromatography on a silica gel column by eluting with n-hexane/ethyl acetate 4:6. 1.9 g of product are obtained.

$^1$H-NMR (CDCl$_3$): δ a 3.55 (bs, 3H, NCH$_3$); 6.38 (s, 1H, CH uracil); 7.4-7.7 (m, 3H, aromatic).

Example 11

Preparation of 3-[4-chloro-3-(tetrazol-5-yl)phenyl]-1-methyl-6-(trifluoromethyl)-2,4(1H,3H)-pyrimidinedione (Compound No 12)

Trimethylsilyl azide (1.34 g) and dibutyltin oxide (0.3 g) are added to a suspension of 2-chloro-5-[1,2,3,6-tetrahydro-3-methyl-2,6-dioxo-4-(trifluoromethyl)pyrimidin-1-yl]benzonitrile (1.9 g) in toluene (15 ml).

The reaction mixture is refluxed for 8 hours. After evaporation of the solvent, the residue is treated with methanol (30 ml) and concentrated in vacuo. The raw product obtained (2.3 g) is purified by digestion with n-hexane (30 ml) at room temperature for 1 hour. 2.1 g of product are obtained having a melting point >180° C. (dec.).

$^1$H-NMR (CDCl$_3$): δ a 3.51 (bs, 3H, NCH$_3$); 6.39 (s, 1H, CH uracil); 7.5-8.0 (m, 3H, aromatic).

$^{19}$F-NMR (CDCl$_3$): δ a −64, 1 (s, 3F, CF$_3$).

Example 12

Preparation of 3-[4-chloro-3-(2-methyl-2H-tetrazol-5-yl)phenyl]-1-methyl-6-(trifluoromethyl)-2,4(1H,3H)-pyrimidinedione (Compound No 13) and 3-[4-chloro-3-(1-methyl-1H-tetrazol-5-yl)phenyl]-1-methyl-6-(trifluoro methyl)-2,4(1H,3H)-pyrimidinedione (Compound No 14)

Methyl iodide (1.22 g) is added to a mixture of 3-[4-chloro-3-(tetrazol-5-yl)phenyl]-1-methyl-6-(trifluoromethyl)-2,4(1H,3H)-pyrimidinedione (1.6 g), obtained in the previous example 10, and potassium carbonate (0.89 g) in acetone (30 ml). The reaction mixture is refluxed for 2 hours. After the evaporation of the solvent, water is added (100 ml) and the mixture is extracted with ethyl acetate (2×50 ml); the organic phase is dried with sodium sulphate and concentrated under vacuum. The residue is purified by chromatography on a silica gel column by eluting with n-hexane/ethyl acetate 4:6. The following compounds are obtained: 0.55 g of 3-[4-chloro-3-(2-methyl-2H-tetrazol-5-yl)phenyl]-1-methyl-6-(trifluoromethyl)-2,4(1H,3H)-pyrimidinedione having a melting point of 192° C.

$^1$H-NMR (CDCl$_3$): δ a 3.54 (bs, 3H, NCH$_3$ uracil); 4.42 (bs, 3H, NCH$_3$ tetrazole); 6.36 (s, 1H, CH uracil); 7.23-7.94 (m, 3H, aromatic);

and 0.3 g of 3-[4-chloro-3-(1-methyl-1H-tetrazol-5-yl)phenyl]-1-methyl-6-(trifluoromethyl)-2,4(1H,3H)-pyrimidinedione having a melting point of 185° C.

$^1$H-NMR (CDCl$_3$): δ a 3.54 (bs, 3H, NCH$_3$ uracil); 4.04 (bs, 3H, NCH$_3$ tetrazole); 6.36 (s, 1H, CH uracil); 7.2-7.7 (m, 3H, aromatic).

The assignment of the structures was effected on the basis of the NMR spectra.

Example 13

The following compounds (identified by elemental analysis, $^1$H- and $^{19}$F-NMR) were prepared, following the procedure described in example 12:

3-[4-chloro-3-(2-ethyl-2H-tetrazol-5-yl)phenyl]-1-methyl-6-(trifluoromethyl)-2,4(1H,3H)-pyrimidinedione (Compound No 15) m.p. 136° C.;

3-[4-chloro-3-(1-ethyl-1H-tetrazol-5-yl)phenyl]-1-methyl-6-(trifluoromethyl)-2,4(1H,3H)-pyrimidinedione (Compound No 16) m.p. 202° C.;

methyl (5-{2-chloro-5-[1,2,3,6-tetrahydro-3-methyl-2,6-dioxo-4-(trifluoromethyl)pyrimidin-1-yl]phenyl}-2H-tetrazol-2-yl)acetate (Compound No 17) m.p. 172° C.;

methyl (5-{2-chloro-5-[1,2,3,6-tetrahydro-3-methyl-2,6-dioxo-4-(trifluoromethyl)pyrimidin-1-yl]phenyl}-1H-tetrazol-1-yl)acetate (Compound No 18) m.p. 130° C.

Example 14

Preparation of N-[4-chloro-3-(4,5-dimethyl-1,3-thiazol-2-yl)phenyl]-4,4,4-trifluoro-3-oxobutaneamide Ethyl trifluoroacetoacetate (2.54 g) is added to a solution of 2-(5-amino-2-chlorophenyl)-4,5-dimethyl-1,3-thiazole (2.20 g) in 110 ml of toluene; a catalytic amount of 4-dimethylaminopyridine is added, then the mixture is heated to 110° C. while distilling off the solvent. When reaction is complete, the residue is concentrated under vacuum; 3.80 g of product are obtained.

Example 15

Preparation of 3-amino-N-[4-chloro-3-(4,5-dimethyl-1,3-thiazol-2-yl)phenyl]-4,4,4-trifluorobut-2-eneamide A mixture of N-[4-chloro-3-(4,5-dimethyl-1,3-thiazol-2-yl)phenyl]-4,4,4-trifluoro-3-oxobutaneamide (3.80 g) and ammonium acetate (6.22 g) in 35 ml of ethyl acetate is refluxed for 7 hours, then cooled to room temperature and diluted with ethyl acetate (70 ml). The mixture is washed once with water and once with brine, then dried over sodium sulphate and concentrated under vacuum.

The residue is purified by chromatography on a silica gel column by eluting with n-hexane/ethyl acetate 9:1; 1.70 g of product are obtained.

Example 16

Preparation of 3-[4-chloro-3-(4,5-dimethyl-1,3-thiazol-2-yl)phenyl]-6-(trifluoromethyl)-2,4(1H,3H)-pyrimidinedione (Compound No 19)

A solution of 3-amino-N-[4-chloro-3-(4,5-dimethyl-1,3-thiazol-2-yl)phenyl]-4,4,4-trifluorobut-2-eneamide (1.70 g), pyridine (0.89 g) and a catalytic amount of 4-dimethylaminopyridine in 61 ml of toluene is heated at 40° C., then a solution of diphosgene (2.24 g) in 4 ml of toluene is added dropwise.

The mixture is kept at 40° C. for 2 hours, then poured into water (100 ml) and extracted with ethyl acetate (3×50 ml); the combined organic phases are washed once with water and once with brine, then dried over sodium sulphate and concentrated under vacuum. 2.00 g of product are obtained.

Example 17

Preparation of 3-[4-chloro-3-(4,5-dimethyl-1,3-thiazol-2-yl)phenyl]-1-methyl-6-(trifluoromethyl)-2,4(1H,3H)-pyrimidinedione (Compound No 20)

Methyl iodide (0.84 g) is added to a mixture of 3-[4-chloro-3-(4,5-dimethyl-1,3-thiazol-2-yl)phenyl]-6-(trifluoromethyl)-2,4(1H,3H)-pyrimidinedione (0.40 g), obtained in the previous example 16, and sodium bicarbonate (0.17 g) in acetone (5 ml). The reaction mixture is refluxed for 2 hours. Water is added (20 ml) after the evaporation of the solvent, and the mixture is extracted with ethyl acetate (3×20 ml); the organic phase is dried with sodium sulphate and concentrated under vacuum. The residue is purified by chromatography on a silica gel column by eluting with n-hexane/ethyl acetate 8:2. 0.21 g of product are obtained, having a melting point of 200° C.

$^1$H-NMR (CDCl$_3$): δ 2.36 (s, 3H, thiazole-CH$_3$), 2.416 (s, 3H, thiazole-CH$_3$), 3.54 (bs, 1H, NCH$_3$); 6.36 (s, 1H, CH uracil); 7.13 (dd, 1H, aromatic); 7.58 (d, 1H, aromatic), 8.18 (d, 1H, aromatic).

Example 18

The following compounds (identified by $^1$H- and $^{19}$F-NMR elemental analysis) were prepared following suitable procedures, some of which are described in the previous examples:

methyl (2E)-4-{2-chloro-4-fluoro-5-[1,2,3,6-tetrahydro-3-methyl-2,6-dioxo-4-(trifluoromethyl)pyrimidin-1-yl]phenylthio}-3-methoxybut-2-enoate (Compound No 21);

methyl (2E)-4-{2,4-dichloro-5-[1,2,3,6-tetrahydro-3-methyl-2,6-dioxo-4-(trifluoromethyl)pyrimidin-1-yl]phenylthio}-3-methoxybut-2-enoate (Compound No 22);

isopropyl (2E)-4-{2-chloro-4-fluoro-5-[1,2,3,6-tetrahydro-3-methyl-2,6-dioxo-4-(trifluoromethyl)pyrimidin-1-yl]phenoxy}-3-methoxybut-2-enoate (Compound N° 23);

methyl (2E)-4-{2,4-dichloro-5-[1,2,3,6-tetrahydro-2,6-dioxo-4-(trifluoromethyl)pyrimidin-1-yl]phenoxy}-3-methoxybut-2-enoate (Compound No 24);

ethyl (2E)-4-{2-chloro-4-fluoro-5-[1,2,3,6-tetrahydro-2,6-dioxo-4-(trifluoromethyl)pyrimidin-1-yl]phenoxy}-3-ethoxybut-2-enoate (Compound No 25);

ethyl (2E)-4-{2,4-dichloro-5-[1,2,3,6-tetrahydro-2,6-dioxo-4-(trifluoromethyl)pyrimidin-1-yl]phenoxy}-3-ethoxybut-2-enoate (Compound No 26);

2,2,2-trifluoroethyl (2E)-4-{2-chloro-4-fluoro-5-[1,2,3,6-tetrahydro-2,6-dioxo-4-(trifluoromethyl)pyrimidin-1-yl]phenoxy}-3-methoxybut-2-enoate (Compound No 27);

(2E)-4-{2-chloro-4-fluoro-5-[1,2,3,6-tetrahydro-2,6-dioxo-4-(trifluoromethyl)pyrimidin-1-yl]phenoxy}-3-methoxy-N,N-dimethylbut-2-enamide (Compound No 28);

S-ethyl (2E)-4-{2-chloro-4-fluoro-5-[1,2,3,6-tetrahydro-2,6-dioxo-4-(trifluoromethyl)pyrimidin-1-yl]phenoxy}-3-methoxybut-2-enethioate (Compound No 29);

isopropyl (2E)-4-{2,4-dichloro-5-[1,2,3,6-tetrahydro-3-methyl-2,6-dioxo-4-(trifluoromethyl)pyrimidin-1-yl]phenoxy}-3-methoxybut-2-enoate (Compound No 30);

2,2,2-trifluoroethyl (2E)-4-{2-chloro-4-fluoro-5-[1,2,3,6-tetrahydro-3-methyl-2,6-dioxo-4-(trifluoromethyl)pyrimidin-1-yl]phenoxy}-3-methoxybut-2-enoate (Compound No 31);

2,2,2-trifluoroethyl (2E)-4-[2,4-dichloro-5-[(1,2,3,6-tetrahydro-3-methyl-2,6-dioxo-4-(trifluoromethyl)pyrimidin-1-yl]phenoxy]-3-methoxybut-2-enoate (Compound No 32);

S-ethyl (2E)-4-{2-chloro-4-fluoro-5-[1,2,3,6-tetrahydro-3-methyl-2,6-dioxo-4-(trifluoromethyl) pyrimidin-1-yl]phenoxy}-3-methoxybut-2-enethioate (Compound No 33);

S-ethyl (2E)-4-{2,4-dichloro-5-[1,2,3,6-tetrahydro-3-methyl-2,6-dioxo-4-(trifluoromethyl)pyrimidin-1-yl]phenoxy}-3-methoxybut-2-enethioate (Compound No 34);

(2E)-4-{(2-chloro-4-fluoro-5-[1,2,3,6-tetrahydro-3-methyl-2,6-dioxo-4-(trifluoromethyl)pyrimidin-1-yl]phenoxy}-3-methoxy-N,N-dimethylbut-2-enamide (Compound No 35);

(2E)-4-{2,4-dichloro-5-[1,2,3,6-tetrahydro-3-methyl-2,6-dioxo-4-(trifluoromethyl)pyrimidin-1-yl]phenoxy}-3-methoxy-N,N-dimethylbut-2-enamide (Compound No 36);

(2E)-4-{2-chloro-4-fluoro-5-[1,2,3,6-tetrahydro-3-methyl-2,6-dioxo-4-(trifluoromethyl)pyrimidin-1-yl]phenylthio}-3-methoxy-N,N-dimethylbut-2-enamide (Compound No 37);

(2E)-4-{2,4-dichloro-5-[1,2,3,6-tetrahydro-3-methyl-2,6-dioxo-4-(trifluoromethyl)pyrimidin-1-yl]phenylthio}-3-methoxy-N,N-dimethylbut-2-enamide (Compound No 38);

3-[4-chloro-2-fluoro-5-(tetrazol-5-ylmethoxy)phenyl]-6-(trifluoromethyl)-2,4(1H,3H)-pyrimidinedione (Compound No 39);

3-{4-chloro-2-fluoro-5-[(2-methyl-2H-tetrazol-5-yl)methoxy]phenyl}-6-(trifluoromethyl)-2,4(1H,3H)-pyrimidinedione (Compound No 40);

3-[2,4-dichloro-5-(tetrazol-5-ylmethoxy)phenyl]-1-methyl-6-(trifluoromethyl)-2,4(1H,3H)-pyrimidinedione (Compound No 41);

3-{4-chloro-2-fluoro-5-[(2-methyl-2H-tetrazol-5-yl) methoxy]phenyl}-1-methyl-6-(trifluoromethyl)-2,4(1H,3H)-pyrimidinedione (Compound No 42), m.p. 167° C.;

3-{2,4-dichloro-5-[(2-methyl-2H-tetrazol-5-yl)methoxy]phenyl}-1-methyl-6-(trifluoromethyl)-2,4(1H,3H)-pyrimidinedione (Compound No 43);

3-{2,4-dichloro-5-[(2-ethyl-2H-tetrazol-5-yl)methoxy]phenyl}-1-methyl-6-(trifluoromethyl)-2,4(1H,3H)-pyrimidinedione (Compound No 44);

3-{2,4-dichloro-5-[(1-ethyl-1H-tetrazol-5-yl)methoxy]phenyl}-1-methyl-6-(trifluoromethyl)-2,4(1H,3H)-pyrimidinedione (Compound No 45);

methyl [5-({2,4-dichloro-5-[1,2,3,6-tetrahydro-3-methyl-2,6-dioxo-4-(trifluoromethyl)pyrimidin-1-yl] phenoxy}methyl)-1H-tetrazol-1-yl]acetate (Compound No 46);

methyl [5-({2,4-dichloro-5-[1,2,3,6-tetrahydro-3-methyl-2,6-dioxo-4-(trifluoromethyl)pyrimidin-1-yl] phenoxy}methyl)-2H-tetrazol-2-yl]acetate (Compound No 47);

3-[4-chloro-3-(tetrazol-5-yl)phenyl]-6-(trifluoromethyl)-2,4(1H,3H)-pyrimidinedione (Compound No 48);

3-[4-chloro-3-(2-methyl-2H-tetrazol-5-yl)phenyl]-6-(trifluoromethyl)-2,4(1H,3H)-pyrimidinedione (Compound No 49);

3-[4-chloro-3-(1-methyl-1H-tetrazol-5-yl)phenyl]-6-(trifluoromethyl)-2,4(1H,3H)-pyrimidinedione (Compound No 50);

3-[4-chloro-2-fluoro-5-(tetrazol-5-yl)phenyl]-6-(trifluoromethyl)-2,4(1H,3H)-pyrimidinedione (Compound No 51);

3-[2,4-dichloro-5-(tetrazol-5-yl)phenyl]-6-(trifluoromethyl)-2,4(1H,3H)-pyrimidinedione (Compound No 52);

3-[4-chloro-2-fluoro-5-(tetrazol-5-yl)phenyl]-1-methyl-6-(trifluoromethyl)-2,4(1H,3H)-pyrimidinedione (Compound No 53);

3-[2,4-dichloro-5-(tetrazol-5-yl)phenyl]-1-methyl-6-(trifluoromethyl)-2,4(1H,3H)-pyrimidinedione (Compound No 54);

3-[4-chloro-2-fluoro-5-(2-methyl-2H-tetrazol-5-yl)phenyl]-6-(trifluoromethyl)-2,4(1H,3H)-pyrimidinedione (Compound No 55);

3-[2,4-dichloro-5-(2-methyl-2H-tetrazol-5-yl)phenyl]-6-(trifluoromethyl)-2,4(1H,3H)-pyrimidinedione (Compound No 56);

3-[4-chloro-2-fluoro-5-(1-methyl-1H-tetrazol-5-yl)phenyl]-6-(trifluoromethyl)-2,4(1H,3H) pyrimidinedione (Compound No 57);

3-[2,4-dichloro-5-(1-methyl-1H-tetrazol-5-yl)phenyl]-6-(trifluoromethyl)-2,4(1H,3H)-pyrimidinedione (Compound No 58);

3-[(4-chloro-2-fluoro-5-(2-methyl-2H-tetrazol-5-yl)phenyl]-1-methyl-6-(trifluoromethyl)-2,4(1H,3H)-pyrimidinedione (Compound No 59);

3-[2,4-dichloro-5-(2-methyl-2H-tetrazol-5-yl)phenyl]-1-methyl-6-(trifluoromethyl)-2,4(1H,3H)-pyrimidinedione (Compound No 60);

3-[4-chloro-2-fluoro-5-(1-methyl-1H-tetrazol-5-yl)phenyl]-1-methyl-6-(trifluoromethyl)-2,4(1H,3H)-pyrimidinedione (Compound No 61);

3-[2,4-dichloro-5-(1-methyl-1H-tetrazol-5-yl)phenyl]-1-methyl-6-(trifluoromethyl)-2,4(1H,3H)-pyrimidinedione (Compound No 62);

methyl (5-{2-chloro-4-fluoro-5-[1,2,3,6-tetrahydro-3-methyl-2,6-dioxo-4-(trifluoromethyl)pyrimidin-1-yl]phenyl}-1H-tetrazol-1-yl) acetate (Compound No 63);

methyl (5-{2-chloro-4-fluoro-5-[(1,2,3,6-tetrahydro-3-methyl-2,6-dioxo-4-(trifluoromethyl)pyrimidin-1-yl]phenyl}-2H-tetrazol-2-yl)acetate (Compound No 64);

methyl (5-{2,4-dichloro-5-[1,2,3,6-tetrahydro-3-methyl-2,6-dioxo-4-(trifluoromethyl)pyrimidin-1-yl]phenyl}-1H-tetrazol-1-yl)acetate (Compound No 65);

methyl (5-{2,4-dichloro-5-[1,2,3,6-tetrahydro-3-methyl-2,6-dioxo-4-(trifluoromethyl)pyrimidin-1-yl]phenyl}-2H-tetrazol-2-yl)acetate (Compound No 66);

3-[4-chloro-3-(4-methoxy-5-methyl-1,3-thiazol-2-yl)phenyl-6-(trifluoromethyl)-2,4(1H,3H)-pyrimidinedione (Compound No 67);

3-[2,4-dichloro-5-(4-methoxy-5-methyl-1,3-thiazol-2-yl)phenyl-6-(trifluoromethyl)-2,4(1H,3H)-pyrimidinedione (Compound No 68);

3-[4-chloro-2-fluoro-5-(4-methoxy-5-methyl-1,3-thiazol-2-yl)phenyl-6-(trifluoromethyl)-2,4(1H,3H)-pyrimidinedione (Compound No 69);

3-[4-chloro-3-(4-methoxy-5-methyl-1,3-thiazol-2-yl)phenyl-1-methyl-6-(trifluoromethyl)-2,4(1H,3H)-pyrimidinedione (Compound No 70), m.p. 201° C.;

3-[4-chloro-3-(4-ethoxy-5-methyl-1,3-thiazol-2-yl)phenyl-1-methyl-6-(trifluoromethyl)-2,4(1H,3H)-pyrimidinedione (Compound No 71);

3-[2,4-dichloro-5-(4-methoxy-5-methyl-1,3-thiazol-2-yl)phenyl-1-methyl-6-(trifluoromethyl)-2,4(1H,3H)-pyrimidinedione (Compound No 72);

3-[2,4-dichloro-5-(4-ethoxy-5-methyl-1,3-thiazol-2-yl)phenyl-1-methyl-6-(trifluoromethyl)-2,4(1H,3H)-pyrimidinedione (Compound No 73);

3-[4-chloro-2-fluoro-5-(4-methoxy-5-methyl-1,3-thiazol-2-yl)phenyl-1-methyl-6-(trifluoromethyl)-2,4(1H,3H)-pyrimidinedione (Compound No 74);

3-[4-chloro-2-fluoro-5-(4-ethoxy-5-methyl-1,3-thiazol-2-yl)phenyl-1-methyl-6-(trifluoromethyl)-2,4(1H,3H)-pyrimidinedione (Compound No 75);

3-[4-chloro-3-(4-benzyloxy-5-methyl-1,3-thiazol-2-yl)phenyl-1-methyl-6-(trifluoromethyl)-2,4(1H,3H)-pyrimidinedione (Compound No 76);

3-[2,4-dichloro-5-(4-benzyloxy-5-methyl-1,3-thiazol-2-yl)phenyl-1-methyl-6-(trifluoromethyl)-2,4(1H,3H)-pyrimidinedione (Compound No 77);

3-[4-chloro-2-fluoro-5-(4-benzyloxy-5-methyl-1,3-thiazol-2-yl)phenyl-1-methyl-6-(trifluoromethyl)-2,4(1H,3H)-pyrimidinedione (Compound No 78);

3-(2,4-dichloro-5-{[5-(trifluoromethyl)-1,3,4-thiadiazol-2-yl]oxy}phenyl)-6-(trifluoromethyl)-2,4(1H,3H)-pyrimidinedione (Compound No 79);

3-(4-chloro-2-fluoro-5-{[5-(trifluoromethyl)-1,3,4-thiadiazol-2-yl]oxy}phenyl)-6-(trifluoromethyl)-2,4(1H,3H)-pyrimidinedione (Compound No 80);

3-(2,4-dichloro-5-{[5-(trifluoromethyl)-1,3,4-oxadiazol-2-yl]oxy}phenyl)-6-(trifluoromethyl)-2,4(1H,3H)-pyrimidinedione (Compound No 81);

3-(4-chloro-2-fluoro-5-{[5-(trifluoromethyl)-1,3,4-oxadiazol-2-yl]oxy}phenyl)-6-(trifluoromethyl)-2,4(1H,3H)-pyrimidinedione (Compound No 82);

3-(4-chloro-3-{[5-(trifluoromethyl)-1,3,4-thiadiazol-2-yl]oxy}phenyl)-1-methyl-6-(trifluoromethyl)-2,4(1H,3H)-pyrimidinedione (Compound No 83);

3-(2,4-dichloro-5-{[5-(trifluoromethyl)-1,3,4-thiadiazol-2-yl]oxy}phenyl)-1-methyl-6-(trifluoromethyl)-2,4(1H,3H)-pyrimidinedione (Compound No 84), m.p. 90° C.;

3-(4-chloro-2-fluoro-5-{[5-(trifluoromethyl)-1,3,4-thiadiazol-2-yl]oxy}phenyl)-1-methyl-6-(trifluoromethyl)-2,4(1H,3H)-pyrimidinedione (Compound No 85), m.p. 4 g° C.;

3-(4-chloro-3-{[5-methyl-1,3,4-thiadiazol-2-yl]oxy}phenyl)-1-methyl-6-(trifluoromethyl)-2,4(1H,3H)-pyrimidinedione (Compound No 86);

3-(2,4-dichloro-5-{[(5-methyl-1,3,4-thiadiazol-2-yl)oxy]phenyl}-1-methyl-6-(trifluoromethyl)-2,4(1H,3H)-pyrimidinedione (Compound No 87);

3-{4-chloro-2-fluoro-5-[(5-methyl-1,3,4-thiadiazol-2-yl)oxy}phenyl]-1-methyl-6-(trifluoromethyl)-2,4(1H,3H)-pyrimidinedione (Compound No 88);

3-(4-chloro-3-{[5-(trifluoromethyl)-1,3,4-oxadiazol-2-yl]oxy}phenyl)-1-methyl-6-(trifluoromethyl)-2,4(1H,3H)-pyrimidinedione (Compound No 89);

3-(2,4-dichloro-3-{[5-(trifluoromethyl)-1,3,4-oxadiazol-2-yl]oxy}phenyl)-1-methyl-6-(trifluoromethyl)-2,4(1H,3H)-pyrimidinedione (Compound No 90);

3-(4-chloro-2-fluoro-5-{[5-(trifluoromethyl)-1,3,4-oxadiazol-2-yl]oxy}phenyl)-1-methyl-6-(trifluoromethyl)-2,4(1H,3H)-pyrimidinedione (Compound No 91);

3-{4-chloro-3-[(5-methyl-1,3,4-oxadiazol-2-yl)oxy]phenyl}-1-methyl-6-(trifluoromethyl)-2,4(1H,3H)-pyrimidinedione (Compound No 92);

3-{2,4-dichloro-5-[(5-methyl-1,3,4-oxadiazol-2-yl)oxy]phenyl}-1-methyl-6-(trifluoromethyl)-2,4(1H,3H)-pyrimidinedione (Compound No 93);

3-{4-chloro-2-fluoro-5-[(5-methyl-1,3,4-oxadiazol-2-yl)oxy]phenyl}-1-methyl-6-(trifluoromethyl)-2,4(1H,3H)-pyrimidinedione (Compound No 94);

methyl (2E)-4-{2-chloro-4-fluoro-5-[1,2,3,6-tetrahydro-3-methyl-6-oxo-2-thioxo-4-(trifluoromethyl)pyrimidin-1-yl]phenoxy}-3-methoxybut-2-enoate (Compound No 95);

methyl (2E)-4-{2-chloro-4-fluoro-5-[1,2,3,6-tetrahydro-3-difluoromethyl-2,6-dioxo-4-(trifluoromethyl)pyrimidin-1-yl]phenoxy}-3-methoxybut-2-enoate (Compound No 96).

methyl (2E)-4-{2,4-dichloro-5-[1,2,3,6-tetrahydro-3-methyl-2,6-dioxo-4-(trifluoromethyl)pyrimidin-1-yl]phenoxy}-3-methoxypent-2-enoate (Compound No 97);

methyl (2E)-4-{2-chloro-4-fluoro-5-[1,2,3,6-tetrahydro-3-methyl-2,6-dioxo-4-(trifluoromethyl)pyrimidin-1-yl]phenoxy}-3-methoxypent-2-enoate (Compound No 98);

ethyl (2E)-4-{2,4-dichloro-5-[1,2,3,6-tetrahydro-3-methyl-2,6-dioxo-4-(trifluoromethyl)pyrimidin-1-yl]phenoxy}-3-methoxybut-2-enoate (Compound No 99), m.p. 128° C.;

ethyl (2E)-4-{2-chloro-4-fluoro-5-[1,2,3,6-tetrahydro-3-methyl-2,6-dioxo-4-(trifluoromethyl)pyrimidin-1-yl]phenoxy}-3-methoxybut-2-enoate (Compound No 100), m.p. 78° C.;

3-{4-chloro-3-[2-(methoxymethyl)-2H-tetrazol-5-yl]phenyl}-1-methyl-6-(trifluoromethyl)-2,4(1H,3H)-pyrimidinedione (Compound No 101), m.p. 80° C.;

3-{4-chloro-3-[1-(methoxymethyl)-1H-tetrazol-5-yl]phenyl}-1-methyl-6-(trifluoromethyl)-2,4(1H,3H)-pyrimidinedione (Compound No 102), m.p. 182° C.;

3-{4-chloro-3-[2-(ethoxymethyl)-2H-tetrazol-5-yl]phenyl}-1-methyl-6-(trifluoromethyl)-2,4(1H,3H)-pyrimidinedione (Compound No 103), m.p. 140° C.;

3-{4-chloro-3-[1-(ethoxymethyl)-1H-tetrazol-5-yl]phenyl}-1-methyl-6-(trifluoromethyl)-2,4(1H,3H)-pyrimidinedione (Compound No 104), m.p. 157° C.;

3-[3-(2-allyl-2H-tetrazol-5-yl)-4-chlorophenyl]-1-methyl-6-(trifluoromethyl)-2,4(1H,3H)-pyrimidinedione (Compound No 105), m.p. 116° C.;

3-[3-(1-allyl-1H-tetrazol-5-yl)-4-chlorophenyl]-1-methyl-6-(trifluoromethyl)-2,4(1H,3H)-pyrimidinedione (Compound No 106), m.p. 160° C.;

3-{4-chloro-2-fluoro-5-[(3-methylisoxazol-5-yl)methoxy]phenyl}-1-methyl-6-(trifluoromethyl)-2,4(1H,3H)-pyrimidinedione (Compound No 107), m.p. 154° C.;

3-{2,4-dichloro-5-[(3-methylisoxazol-5-yl)methoxy]phenyl}-1-methyl-6-(trifluoromethyl)-2,4(1H,3H)-pyrimidinedione (Compound No 108), m.p. 185° C.;

3-[4-chloro-3-(4-isopropoxy-5-methyl-1,3-thiazol-2-yl)phenyl-1-methyl-6-(trifluoromethyl)-2,4(1H,3H)-pyrimidinedione (Compound No 109), m.p. 124° C.;

3-[4-chloro-3-(4-hydroxy-5-methyl-1,3-thiazol-2-yl)phenyl-1-methyl-6-(trifluoromethyl)-2,4(1H,3H)-pyrimidinedione (Compound No 110), m.p. 165° C.;

3-{4-chloro-2-fluoro-5-[(5-methyl-1,2,4-oxadiazol-3-yl)methoxy]phenyl}-1-methyl-6-(trifluoromethyl)-2,4(1H,3H)-pyrimidinedione (Compound No 111);

3-{2,4-dichloro-5-[(5-methyl-1,2,4-oxadiazol-3-yl)methoxy]phenyl}-1-methyl-6-(trifluoromethyl)-2,4(1H,3H)-pyrimidinedione (Compound No 112), m.p. 167° C.;

3-[3-(1,3-benzothiazol-2-yl)-4-chlorophenyl]-1-methyl-6-(trifluoromethyl)-2,4(1H,3H)-pyrimidinedione (Compound No 113), m.p. 189° C.;

3-[3-(1,3-benzoxazol-2-yl)-4-chlorophenyl]-1-methyl-6-(trifluoromethyl)-2,4(1H,3H)-pyrimidinedione (Compound No 114), m.p. 183° C.;

3-{4-chloro-2-fluoro-5-[(3-methyl-1,2,4-oxadiazol-5-yl)methoxy]phenyl}-1-methyl-6-(trifluoromethyl)-2,4(1H,3N)-pyrimidinedione (Compound No 115), m.p. 60° C.;

3-[4-chloro-3-(4-methyl-1,3-thiazol-2-yl)phenyl-1-methyl-6-(trifluoromethyl)-2,4(1H,3H)-pyrimidinedione (Compound No 116);

3-[4-chloro-2-fluoro-5-(1,2,4-oxadiazol-3-ylmethoxy)phenyl]-1-methyl-6-(trifluoromethyl)-2,4(1H,3H)-pyrimidinedione (Compound No 117), m.p. 122° C.;

3-[3-(2-tert-butyl-2H-tetrazol-5-yl)-4-chlorophenyl]-1-methyl-6-(trifluoromethyl)-2,4(1H,3H)-pyrimidinedione (Compound No 118), m.p. 154° C.;

3-[5-(1,3-benzothiazol-2-yl)-4-chloro-2-fluorophenyl]-1-methyl-6-(trifluoromethyl)-2,4(1H,3H)-pyrimidinedione (Compound No 119), m.p. 211° C.;

3-(4-chloro-3-{2-[(2-methoxyethoxy)methyl]-2H-tetrazol-5-yl}phenyl)-1-methyl-6-(trifluoromethyl)-2,4(1H,3H)-pyrimidinedione (Compound No 120);

3-(4-chloro-3-{1-[(2-methoxyethoxy)methyl]-1H-tetrazol-5-yl}phenyl)-1-methyl-6-(trifluoromethyl)-2,4(1H,3H)-pyrimidinedione (Compound No 121);

3-[5-(1,3-benzoxazol-2-yl)-4-chloro-2-fluorophenyl]-1-methyl-6-(trifluoromethyl)-2,4(1H,3H)-pyrimidinedione (Compound No 122), m.p. 178° C.;

3-[5-(1,3-benzothiazol-2-yl)-2,4-dichlorophenyl]-1-methyl-6-(trifluoromethyl)-2,4(1H,3H)-pyrimidinedione (Compound No 123), m.p. 195° C.;

3-[2,4-dichloro-5-(6-methyl-1,3-benzoxazol-2-yl)phenyl]-1-methyl-6-(trifluoromethyl) 2,4(1H,3H)-pyrimidinedione (Compound No 124), m.p. 200° C.;

2-(5-{2-chloro-5-[1,2,3,6-tetrahydro-3-methyl-2,6-dioxo-4-(trifluoromethyl)pyrimidin-1-yl]phenyl}-2H-tetrazol-2-yl)-N,N-dimethylacetamide (Compound No 125) m.p. 208° C.;

2-(5-{2-chloro-5-[1,2,3,6-tetrahydro-3-methyl-2,6-dioxo-4-(trifluoromethyl)pyrimidin-1-yl]phenyl}-2H-tetrazol-2-yl)acetamide (Compound No 126) m.p. 200° C.;

3-[2,4-dichloro-5-(4-methyl-1,3-thiazol-2-yl)phenyl-1-methyl-6-(trifluoromethyl)-2,4(1H,3H)-pyrimidinedione (Compound No 127), m.p. 188° C.;

3-[(3-(4-tert-butyl-1,3-thiazol-2-yl)-4-chlorophenyl]-1-methyl-6-(trifluoromethyl) 2,4(1H,3H)-pyrimidinedione (Compound No 128), m.p. 173° C.;

3-[2,4-dichloro-5-(4-isobutyl-1,3-thiazol-2-yl)phenyl]-1-methyl-6-(trifluoromethyl) 2,4(1H,3H)-pyrimidinedione (Compound No 129), m.p. 167° C.;

3-[4-chloro-3-(1,3-thiazol-2-yl)phenyl]-1-methyl-6-(trifluoromethyl) 2,4(1H,3H)-pyrimidinedione (Compound No 130);

ethyl 2-{2-chloro-5-[1,2,3,6-tetrahydro-3-methyl-2,6-dioxo-4-(trifluoromethyl)pyrimidin-1-yl]phenyl}-4-methyl-1,3-thiazole-5-carboxylate (Compound No 131), m.p. 200° C.;

3-{5-[(3-tert-butylisoxazol-5-yl)methoxy]-4-chloro-2-fluorophenyl}-1-methyl-6-(trifluoromethyl)-2,4(1H,3H)-pyrimidinedione (Compound No 132), m.p. 142° C.;

3-{4-chloro-2-fluoro-5-[(3-isopropylisoxazol-5-yl)methoxy]phenyl}-1-methyl-6-(trifluoromethyl)-2,4(1H,3H)-pyrimidinedione (Compound No 133), m.p. 128° C.;

3-[4-chloro-3-(2-isopropyl-2H-tetrazol-5-yl)phenyl]-1-methyl-6-(trifluoromethyl)-2,4(1H,3H)-pyrimidinedione (Compound No 134) m.p. 147° C.;

3-[3-(2-benzyl-2H-tetrazol-5-yl)-4-chlorophenyl]-1-methyl-6-(trifluoromethyl)-2,4(1H,3H)-pyrimidinedione (Compound No 135);

3-[3-(1-benzyl-1H-tetrazol-5-yl)-4-chlorophenyl]-1-methyl-6-(trifluoromethyl)-2,4(1H,3H)-pyrimidinedione (Compound No 136);

3-{4-chloro-2-fluoro-5-[(1-methyl-1H-tetrazol-5-yl) oxy]phenyl}-1-methyl-6-(trifluoromethyl)-2,4(1H,3H)-pyrimidinedione (Compound No 137);

3-{4-chloro-2-fluoro-5-[(2-methyl-2H-tetrazol-5-yl)oxy]phenyl}-1-methyl-6-(trifluoromethyl)-2,4(1H,3H)-pyrimidinedione (Compound No 138);

methyl (2E)-4-{2-chloro-5-[1,2,3,6-tetrahydro-3-methyl-2,6-dioxo-4(trifluoromethyl)pyrimidin-1-yl]phenoxy}-3-methoxybut-2-enoate (Compound No 139);

ethyl (2E)-4-{(2-chloro-5-[1,2,3,6-tetrahydro-3-methyl-2,6-dioxo-4(trifluoromethyl)pyrimidin-1-yl]phenoxy}-3-ethoxybut-2-enoate (Compound No 140);

3-[4-chloro-3-(1,2,4-oxadiazol-3-ylmethoxy)phenyl]-1-methyl-6-(trifluoromethyl)-2,4(1H,3H)-pyrimidinedione (Compound No 141);

3-{4-chloro-3-[(3-methylisoxazol-5-yl)methoxy]phenyl}-1-methyl-6-(trifluoromethyl)-2,4(1H,3H)-pyrimidinedione (Compound No 142);

3-[4-chloro-3-(4,5,6,7-tetrahydro-1,3-benzothiazol-2-yl)phenyl]-1-methyl-6-(trifluoromethyl)-2,4(1H,3H)-pyrimidinedione (Compound No 143);

3-[4-chloro-3-(5,6-dihydro-1,4,2-dioxazin-3-yl)phenyl]-1-methyl-6-(trifluoromethyl)-2,4(1H,3H)-pyrimidinedione (Compound No 144);

3-[4-chloro-3-(4-methyl-5-oxo-5,6-dihydro-4H-1,3,4-oxadiazin-2-yl)phenyl]-1-methyl-6-(trifluoromethyl)-2,4(1H,3H)-pyrimidinedione (Compound No 145);

3-[4-chloro-3-(5,6-dihydro-1,4,2-dioxazin-3-ylmethoxy)-2-fluorophenyl]-1-methyl-6-(trifluoromethyl)-2,4(1H,3H)-pyrimidinedione (Compound No 146);

3-{4-chloro-2-fluoro-5-[(4-methyl-5-oxo-5,6-dihydro-4H-1,3,4-oxadiazin-2-yl)methoxy]phenyl}-1-methyl-6-(trifluoromethyl)-2,4(1H,3H)-pyrimldinedione (Compound No 147);

3-[4-chloro-3-(2-phenyl-2H-tetrazol-5-yl)phenyl]-1-methyl-6-(trifluoromethyl)-2,4(1H,3H)-pyrimidinedione (Compound No 148);

3-[4-chloro-3-(1-phenyl-1H-tetrazol-5-yl)phenyl]-1-methyl-6-(trifluoromethyl)-2,4(1H,3H)-pyrimidinedione (Compound No 149);

3-{4-chloro-3-[1-(cyclopropylmethyl)-1H-tetrazol-5-yl]phenyl}-1-methyl-6-(trifluoromethyl)-2,4(1H,3H)-pyrimidinedione (Compound No 150);

3-{4-chloro-3-[2-(cyclopropylmethyl)-2H-tetrazol-5-yl]phenyl}-1-methyl-6-(trifluoromethyl)-2,4(1H,3H)-pyrimidinedione (Compound No 151);

3-{4-chloro-3-[1-(2-oxopropyl)-1H-tetrazol-5-yl]phenyl}-1-methyl-6-(trifluoromethyl)-2,4(1H,3H)-pyrimidinedione (Compound No 152);

3-{4-chloro-3-[2-(2-oxopropyl)-2H-tetrazol-5-yl]phenyl}-1-methyl-6-(trifluoromethyl)-2,4(1H,3H)-pyrimidinedione (Compound No 153);

3-[4-chloro-3-(4-cyclopropyl-1,3-thiazol-2-yl)phenyl]-1-methyl-6-(trifluoromethyl)-2,4(1H,3H)-pyrimidinedione (Compound No 154);

3-{4-chloro-3-[4-(4-chlorophenyl)-1,3-thiazol-2-yl]phenyl}-1-methyl-6-(trifluoromethyl)-2,4(1H,3H)-pyrimidinedione (Compound No 155);

ethyl 2-{2-chloro-5-[1,2,3,6-tetrahydro-3-methyl-2,6-dioxo-4-(trifluoromethyl)pyrimidin-1-yl]phenyl}-1,3-thiazole-4-carboxylate (Compound No 156), m.p. 197° C.;

3-[3-(2-butyl-2H-tetrazol-5-yl)-4-chlorophenyl]-1-methyl-6-(trifluoromethyl)-2,4(1H,3H)-pyrimidinedione (Compound No 157), m.p. 108° C.;

3-[4-chloro-2-fluoro-5-(5,6-dihydro-1,4,2-dioxazin-3-ylmethoxy)-2-fluorophenyl]-1-methyl-6-(trifluoromethyl)-2,4(1H,3H)-pyrimidinedione (Compound No 158);

3-(4-chloro-3-{2-[(4-chlorophenoxy)methyl]-2H-tetrazol-5-yl}phenyl)-1-methyl-6-(trifluoromethyl)-2,4(1H,3H)-pyrimidinedione (Compound No 159);

3-(4-chloro-3-{1-[(4-chlorophenoxy)methyl]-1H-tetrazol-5-yl}phenyl)-1-methyl-6-(trifluoromethyl)-2,4(1H,3H)-pyrimidinedione (Compound No 160);

3-[3-(4-tert-butyl-5-oxo-4,5-dihydro-1,3,4-thiadiazol-2-yl)-4-chlorophenyl]-1-methyl-6-(trifluoromethyl)-2,4(1H,3H)-pyrimidinedione (Compound No 161);

3-{4-chloro-3-[2-(4-chlorobenzyl)-2H-tetrazol-5-yl]phenyl}-1-methyl-6-(trifluoromethyl)-2,4(1H,3H)-pyrimidinedione (Compound No 162);

3-{4-chloro-3-[1-(4-chlorobenzyl)-1H-tetrazol-5-yl]phenyl}-1-methyl-6-(trifluoromethyl)-2,4(1H,3H)-pyrimidinedione (Compound No 163);

methyl 2-{2-chloro-5-[1,2,3,6-tetrahydro-3-methyl-2,6-dioxo-4-(trifluoromethyl)pyrimidin-1-yl]phenyl}-1,3-thiazole-4-carboxylate (Compound No 164);

methyl (2-{2-chloro-5-[1,2,3,6-tetrahydro-3-methyl-2,6-dioxo-4-(trifluoromethyl)pyrimidin-1-yl]phenyl}-1,3-thiazol-4-yl)acetate (Compound No 165).

Example 19

Determination of the Herbicidal Activity and Phytotoxicity in Pre-Emergence

The herbicidal activity of the compounds of the invention in pre-emergence was evaluated according to the following operative procedures.

The vegetable species of interest (weeds or crops) were sown in pots with an upper diameter of 10 cm, a height of 10 cm and containing sandy soil. 10 pots were used for each vegetable species.

Water was added to each pot in such a quantity as to germinate the seeds. The pots were divided into two groups, each containing 5 pots for each weed or crop.

After one day from the sowing, the first set of pots was treated with a hydro-acetonic dispersion containing acetone at 10% in volume, the product under evaluation at the desired concentration and Tween 20 at 0.5%.

The second set was treated with a hydro-acetonic solution only, containing acetone at 10% in volume and Tween 20 at 0.5%, and was used as comparison (blank).

All pots were kept under observation in a conditioned environment under the following conditions:
temperature: 24° C.;
relative humidity: 60%;
photoperiod: 16 ore;
light intensity: 10000 lux.

The pots were uniformly watered in order to ensure a sufficient humidity degree for a good development of the plants.

Fifteen days after the treatment, the herbicidal activity was evaluated on the basis of the following values, which refer to the damage percentage tested on the treated plants, with respect to the non-treated plants (blank):

0=0-10% damage;
1=11-30% damage;
2=31-50% damage;
3=51-70% damage;
4=71-90% damage;
5=91% damage—death of the plant.

Table 1 shows the results obtained by treating the vegetable species listed below with compounds 2, 6 and 13 with a dosage of 15 g/ha:

*Abutilon theofrasti* (AT); *Amaranthus retroflexus* (AR); *Chenopodium album* (CA); *Convolvulus sepium* (CS); *Galium aparine* (GA); *Ipomea purpurea* (IP); *Portulaca oleracea* (PO); *Solanum nigrum* (SN); *Sida spinosa* (SS).

TABLE 1

| Herbicidal activity in pre-emergence with a dosage of 15 g/ha | | | | | | | | | |
| --- | --- | --- | --- | --- | --- | --- | --- | --- | --- |
| Vegetal species | AT | AR | CA | CS | GA | IP | PO | SN | SS |
| Compound No 2 | 5 | 5 | 5 | 5 | 5 | 5 | 5 | 5 | 5 |
| Compound No 6 | 5 | 4 | 5 | — | 5 | 4 | 5 | 5 | 5 |
| Compound No 13 | 5 | 5 | 5 | — | 5 | 5 | 5 | 5 | 5 |

Example 20

Determination of the Herbicidal Activity and Phytotoxicity in Post-Emergence

The herbicidal activity of the compounds of the invention in post-emergence was evaluated according to the following operative procedures.

The vegetable species of interest (weeds or crops) were sown in pots with an upper diameter of 10 cm, a height of 10 cm and containing sandy soil. 10 pots were used for each vegetable species.

Water was added to each pot in such a quantity as to germinate the seeds. The pots were divided into two groups, each containing 5 pots for each weed or crop.

Fifteen days after sowing (ten, in the case of wheat), when the weeds and crops, according to the species, were 10-15 cm high, the first set of pots was treated with a hydro-acetonic dispersion containing acetone at 10% in volume, the product under evaluation at the desired concentration and Tween 20 at 0.5%.

The second set was treated with a hydro-acetonic solution only, containing acetone at 10% in volume and Tween 20 at 0.5%, and was used as comparison (blank).

All pots were kept under observation in a conditioned environment under the following conditions:
temperature: 24° C.;
relative humidity: 60%;
photo-period: 16 ore;
light intensity: 10000 lux.

The pots were uniformly watered every other day so as to ensure a humidity degree sufficient for a good development of the plants.

The herbicidal activity was evaluated fifteen days after the treatment, on the basis of the following values which refer to the percentage of damage tested on the treated plants with respect to the non-treated plants (blank):
0=0-10% damage;
1=11-30% damage;
2=31-50% damage;
3=51-70% damage;
4=71-90% damage;
5=91% damage—death of the plant.

Table 2 shows the results obtained by treating the vegetable species listed below with compounds 2, 6 and 13 with a dosage of 15 g/ha:

*Abutilon theofrasti* (AT); *Amaranthus retroflexus* (AR); *Chenopodium album* (CA); *Convolvulus sepium* (CS); *Galium aparine* (GA); *Ipomea purpurea* (IP); *Portulaca oleracea* (PO); *Solanum nigrum* (SN); *Sida spinosa* (SS).

TABLE 2

| Herbicidal activity in post-emergence with a dosage of 15 g/ha | | | | | | | | | |
|---|---|---|---|---|---|---|---|---|---|
| Vegetable species | AT | AR | CA | CS | GA | IP | PO | SN | SS |
| Compound No 2 | 5 | 5 | 5 | 5 | 5 | 5 | 4 | 5 | 5 |
| Compound No 6 | 5 | 3 | 4 | — | — | 5 | 4 | 5 | 4 |
| Compound No 13 | 5 | 5 | 5 | — | — | 5 | 5 | 5 | 5 |

The invention claimed is:

1. A compound having formula (I):

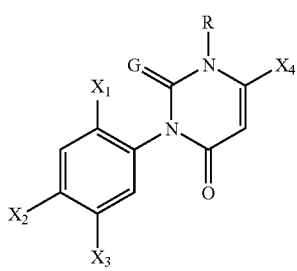

wherein:
$X_1$ represents a hydrogen atom or a halogen atom;
$X_2$ represents a halogen atom;
$X_4$ represents a $C_1$-$C_3$ haloalkyl group;
R represents a hydrogen atom, a $C_1$-$C_3$ alkyl group or a $C_1$-$C_3$ haloalkyl group;
G represents an oxygen atom or a sulphur atom;
$X_3$ represents a Q(CR$_1$R$_2$)$_n$Z— group, a $Q_2$- group, a Y(CO)—CR$_6$=CR$_5$—CR$_3$R$_4$Z— group;
Z represents an oxygen atom or a sulphur atom;
$R_1$, $R_2$, $R_3$ and $R_4$, the same or different, represent a hydrogen atom or, a $C_1$-$C_4$ alkyl group;
$R_5$ represents an OR$_7$ group;
$R_6$ represents a hydrogen atom or a $C_1$-$C_4$ alkyl group;
$R_7$ represents a $C_1$-$C_4$ alkyl group or a $C_1$-$C_4$ haloalkyl group;
Y represents a $C_4$-$C_6$ alkoxy or haloalkoxy group;
n represents 1, 2 or 3;
Q represents a heterocyclic group selected from 1,3,4-oxadiazolyl, 1,3,4-thiadiazolyl, 1,2,4-thiadiazolyl and 1,2,4-oxadiazolyl, said groups, in turn, being optionally substituted with a halogen atom selected from chlorine, fluorine, bromine or iodine, or with a group selected from $C_1$-$C_6$ alkyl or $C_1$-$C_6$ haloalkyl, $C_2$-$C_6$ alkenyl or $C_2$-$C_6$ haloalkenyl, $C_2$-$C_6$ alkynyl or $C_2$-$C_6$ haloalkynyl,
$Q_2$ represents a heterocyclic group selected from 1H-tetrazol-5-yl or 2H-tetrazol-5-yl, being optionally substituted with a group selected from: $C_1$-$C_6$ alkyl; $C_1$-$C_6$ haloalkyl; $C_2$-$C_6$ alkenyl; $C_2$-$C_6$ haloalkenyl; $C_2$-$C_6$ alkynyl; $C_2$-$C_6$ haloalkynyl, $C_2$-$C_6$ alkoxyalkyl; $C_2$-$C_6$ haloalkoxyalkyl; $C_3$-$C_8$ alkoxyalkoxyalkyl, $C_6$-$C_{12}$ arylalkyl, $C_7$-$C_{12}$ aryloxyalkyl, $C_8$-$C_{12}$ arylalkyloxyalkyl said groups in turn being optionally substituted with halogen atoms, $C_1$-$C_4$ alkyl groups, $C_1$-$C_3$ haloalkyl groups, $C_1$-$C_4$ alkoxy groups, $C_1$-$C_3$ haloalkoxy groups, CN; $C_3$-$C_7$ cycloalkyl, $C_6$-$C_{12}$ cycloalkylalkyl, tetrahydropyran-2-yl said groups in turn being optionally substituted with halogen atoms, $C_1$-$C_4$ alkyl groups, $C_1$-$C_4$ alkoxy groups.

2. A compound according to claim 1, characterized in that it is selected from:
methyl (2E)-4-{2-chloro-4-fluoro-5-[1,2,3,6-tetrahydro-3-methyl-2,6-dioxo-4-(trifluoromethyl)pyrimidin-1-yl]phenoxy}-3-methoxybut-2-enoate;
methyl (2E)-4-{2,4-dichloro-5-[1,2,3,6-tetrahydro-3-methyl-2,6-dioxo-4-(trifluoromethyl)pyrimidin-1-yl]phenoxy}-3-methoxybut-2-enoate;
methyl (2E)-4-{2-chloro-4-fluoro-5-[1,2,3,6-tetrahydro-3-methyl-2,6-dioxo-4-(trifluoromethyl)pyrimidin-1-yl]phenylthio}-3-methoxybut-2-enoate;
ethyl (2E)-4-{2-chloro-4-fluoro-5-[1,2,3,6-tetrehydro-3-methyl-2,6-dioxo-4-(trifluoromethyl)pyrimidin-1-yl]phenoxy}-3-ethoxybut-2-enoate;
methyl (2E)-4-{2,4-dichloro-5-[1,2,3,6-tetrahydro-3-methyl-2,6-dioxo-4-(trifluoromethyl)pyrimidin-1-yl]phenylthio}-3-methoxybut-2-enoate;
ethyl (2E)-4-{2,4-dichloro-5-[1,2,3,6-tetrahydro-3-methyl-2,6-dioxo-4-(trifluoromethyl)pyrimidin-1-yl]phenoxy}-3-ethoxybut-2-enoate;
isopropyl (2E)-4-{2-chloro-4-fluoro-5-[1,2,3,6-tetrahydro-3-methyl-2,6-dioxo-4-(trifluoromethyl)pyrimidin-1-yl]phenoxy}-3-methoxybut-2-enoate;
methyl (2E)-4-{2-chloro-4-fluoro-5-[1,2,3,6-tetrahydro-2,6-dioxo-4-(trifluoromethyl)pyrimidin-1-yl]phenoxy}-3-methoxybut-2-enoate;
methyl (2E)-4-{2,4-dichloro-5-[1,2,3,6-tetrahydro-2,6-dioxo-4-(trifluoromethyl)pyrimidin-1-yl]phenoxy}-3-methoxybut-2-enoate;
ethyl (2E)-4-{2-chloro-4-fluoro-5-[1,2,3,6-tetrahydro-2,6-dioxo-4-(trifluoromethyl)pyrimidin-1-yl]phenoxy}-3-ethoxybut-2-enoate;
isopropyl (2E)-4-{2,4-dichloro-5-[1,2,3,6-tetrahydro-3-methyl-2,6-dioxo-4-(trifluoromethyl)pyrimidin-1-yl]phenoxy}-3-methoxybut-2-enoate;
2,2,2-trifluoroethyl (2E)-4-{2-chloro-4-fluoro-5-[1,2,3,6-tetrahydro-3-methyl-2,6-dioxo-4-(trifluoromethyl)pyrimidin-1-yl]phenoxy}-3-methoxybut-2-enoate;
2,2,2-trifluoroethyl (2E)-4-{2,4-dichloro-5-[1,2,3,6-tetrahydro-3-methyl-2,6-dioxo-4-(trifluoromethyl)pyrimidin-1-yl]phenoxy}-3-methoxybut-2-enoate;

3-{5-[(5-tert-butyl-1,3,4-oxadiazol-2-yl)methoxy]-4-chloro-2-fluorophenyl}-1-methyl-6-(trifluoromethyl)-2,4(1H,3H)-pyrimidinedione;

3-[4-chloro-3-(tetrazol-5-yl)phenyl]-6-(trifluoromethyl)-2,4(1H,3H)-pyrimidinedione;

3-[4-chloro-3-(2-methyl-2H-tetrazol-5-yl)phenyl]-6-(trifluoromethyl)-2,4(1H,3H)-pyrimidinedione;

3-[4-chloro-3-(1-methyl-1H-tetrazol-5-yl)phenyl]-6-(trifluoromethyl)-2,4(1H,3H)-pyrimidinedione;

3-[4-chloro-3-(tetrazol-5-yl)phenyl]-1-methyl-6-(trifluoromethyl)-2,4(1H,3H)-pyrimidinedione;

3-[4-chloro-2-fluoro-5-(tetrazol-5-yl)phenyl]-6-(trifluoromethyl)-2,4(1H,3H)-pyrimidinedione;

3-[2,4-dichloro-5-(tetrazol-5-yl)phenyl]-6-(trifluoromethyl)-2,4(1H,3H)-pyrimidinedione;

3-[4-chloro-2-fluoro-5-(tetrazol-5-yl)phenyl]-1-methyl-6-(trifluoromethyl)-2, 4(1H,3H)-pyrimidinedione;

3-[2,4-dichloro-5-(tetrazol-5-yl)phenyl]-1-methyl-6-(trifluoromethyl)-2,4(1H,3H)-pyrimidinedione;

3-[4-chloro-3-(2-methyl-2H-tetrazol-5-yl)phenyl]-1-methyl-6-(trifluoromethyl)-2,4(1H,3H)-pyrimidinedione;

3-[4-chloro-2-fluoro-5-(2-methyl-2H-tetrazol-5-yl)phenyl]-6-(trifluoromethyl)-2, 4 (1H,3H)-pyrimidinedione;

3-[2,4-dichloro-5-(2-methyl-2H-tetrazol-5-yl)phenyl]-6-(trifluoromethyl)-2,4(1H,3H)-pyrimidinedione;

3-[4-chloro-2-fluoro-5-(1-methyl-1H-tetrazol-5-yl)phenyl]-6-(trifluoromethyl)-2,4(1H,3H)-pyrimidinedione;

3-[2,4-dichloro-5-(1-methyl-1H-tetrazol-5-yl)phenyl]-6-(trifluoromethyl)-2,4(1H,3H)-pyrimidinedione;

3-[4-chloro-2-fluoro-5-(2-methyl-2H-tetrazol-5-yl)phenyl]-1-methyl-6-(trifluoromethyl)-2,4(1H,3H)-pyrimidinedione;

3-[2,4-dichloro-5-(2-methyl-2H-tetrazol-5-yl)phenyl]-1-methyl-6-(trifluoromethyl)-2,4(1H,3H)-pyrimidinedione;

3- [4-chloro-3-(2-ethyl-2H-tetrazol-5-yl)phenyl]-1-methyl-6-(trifluoromethyl)-2,4(1H,3H)-pyrimidinedione;

3-[4-chloro-3-(1-methyl-1H-tetrazol-5-yl)phenyl]-1-methyl-6-(trifluoromethyl)-2,4(1H,3H)-pyrimidinedione;

3-[4-chloro-2-fluoro-5-(1-methyl-1H-tetrazol-5-yl)phenyl]-1-methyl-6-(trifluoromethyl)-2,4(1H,3H)-pyrimidinedione;

3-[2,4-dichloro-5-(1-methyl-1H-tetrazol-5-yl)phenyl]-1-methyl-6-(trifluoromethyl)-2,4(1H,3H)-pyrimidinedione;

3-[4-chloro-3-(1-ethyl-1H-tetrazol-5-yl)phenyl]-1-methyl-6-(trifluoromethyl)-2,4(1H,3H)-pyrimidinedione;

methyl (2E)-4-{(2-chloro-4-fluoro-5-[1,2,3,6-tetrahydro-3-methyl-6-oxo-2-thioxo-4-(trifluoromethyl)pyrimidin-1-yl]-phenoxy}-3-methoxybut-2-enoate;

methyl (2E)-4-{2-chloro-4-fluoro-5-[1,2,3,6-tetrahydro-3-difluoromethyl-2,6-dioxo-4-(trifluoromethyl)pyrimidin-1-yl]phenoxy}-3-methoxybut-2-enoate;

methyl(2E)-4-{2,4-dichloro-5-[1,2,3,6-tetrahydro-3-methyl-2,6-dioxo-4-(trifluoromethyl)pyrimidin-1-yl]phenoxy}-3-methoxypent-2-enoate;

methyl(2E)-4-{2-chloro-4-fluoro-5-[1,2,3,6-tetrahydro-3-methyl-2,6-dioxo-4-(trifluoromethyl)pyrimidin-1-yl]phenoxy}-3-methoxypent-2-enoate;

ethyl (2E)-4-{2,4-dichloro-5-[1,2,3,6-tetrahydro-3-methyl-2,6-dioxo-4-(trifluoromethyl)pyrimidin-1-yl]phenoxy}-3-methoxybut-2-enoate;

ethyl (2E)-4-{2-chloro-4-fluoro-5-[1,2,3,6-tetrahydro-3-methyl-2,6-dioxo-4-(trifluoromethyl)pyrimidin-1-yl]phenoxy}-3-methoxybut-2-enoate;

3-{4-chloro-3-[2-(methoxymethyl)-2H-tetrazol-5-yl]phenyl}-1-methyl-6-(trifluoromethyl)-2,4(1H,3H)-pyrimidinedione;

3-{4-chloro-3-[1-(methoxymethyl)-1H-tetrazol-5-yl]phenyl}-1-methyl-6-(trifluoromethyl)-2,4(1H,3H)-pyrimidinedione;

3-{4-chloro-3-[2-(ethoxymethyl)-2H-tetrazol-5-yl]phenyl}-1-methyl-6-(trifluoromethyl)-2,4(1H,3H)-pyrimidinedione;

3-{4-chloro-3-[1-(ethoxymethyl)-1H-tetrazol-5-yl]phenyl}-1-methyl-6-(trifluoromethyl)-2,4(1H,3H)-pyrimidinedione;

3-[3-(2-allyl-2H-tetrazol-5-yl)-4-chlorophenyl]-1-methyl-6-(trifluoromethyl)-2,4(1H,3H)-pyrimidinedione;

3-[3-(1-allyl-1H-tetrazol-5-yl)-4-chlorophenyl]-1-methyl-6-(trifluoromethyl)-2,4(1H,3H)-pyrimidinedione;

3-{4-chloro-2-fluoro-5-[(5-methyl-1,2,4-oxadiazol-3-yl)methoxy]phenyl}-1-methyl-6-(trifluoromethyl)-2,4(1H,3H)-pyrimidinedione;

3-{2,4-dichloro-5-[(5-methyl-1,2,4-oxadiazol-3-yl)methoxy]phenyl}-1-methyl-6-(trifluoromethyl)-2,4(1H,3H)-pyrimidinedione;

3-{4-chloro-2-fluoro-5-[(3-methyl-1,2,4-oxadiazol-5-yl)methoxy]phenyl}-1-methyl-6-(trifluoromethyl)-2,4(1H,3H)-pyrimidinedione;

3-[4-chloro-2-fluoro-5-(1,2,4-oxadiazol-3-ylmethoxy)phenyl]-1-methyl-6-(trifluoromethyl)-2,4(1H,3H)-pyrimidinedione;

3-[3-(2-tert-butyl-2H-tetrazol-5-yl)-4-chlorophenyl]-1-methyl-6-(trifluoromethyl)-2,4(1H,3H)-pyrimidinedione;

3-(4-chloro-3-{2-[(2-methoxyethoxy)methyl]-2H-tetrazol-5-yl}phenyl)-1-methyl-6-(trifluoromethyl)-2,4(1H,3H)-pyrimidinedione;

3-(4-chloro-3-{1-[(2-methoxyethoxy)methyl]-1H-tetrazol-5-yl}phenyl)-1-methyl-6-(trifluoromethyl)-2,4(1H,3H)-pyrimidinedione;

3-[4-chloro-3-(2-isopropyl-2H-tetrazol-5-yl)phenyl]-1-methyl-6-(trifluoromethyl)-2,4(1H,3H)-pyrimidinedione;

3-[3-(2-benzyl-2H-tetrazol-5-yl)-4-chlorophenyl]-1-methyl-6-(trifluoromethyl)-2,4(3H)-pyrimidinedione;

3-[3-(1-benzyl-1H-tetrazol-5-yl)-4-chlorophenyl]-1-methyl-6-(trifluoromethyl)-2,4(1H,3H)-pyrimidinedione;

methyl (2E)-4-{2-chloro-5-[1,2,3,6-tetrahydro-3-methyl-2,6-dioxo-4 (trifluoromethyl)pyrimidin-1-yl]phenoxy}-3-methoxybut-2-enoate;

ethyl (2E)-4-{2-chloro-5-[1,2,3,6-tetrahydro-3-methyl-2, 6-dioxo-4 (trifluoromethyl) pyrimidin-1-yl]phenoxy}-3-ethoxybut-2-enoate;

3-[4-chloro-3-(1,2,4-oxadiazol-3-ylmethoxy)phenyl]-1-methyl-6-(trifluoromethyl)-2,4(1H,3H)-pyrimidinedione;

3-{4-chloro-3-[1-(cyclopropylmethyl)-1H-tetrazol-5-yl]phenyl}-1-methyl-6-(trifluoromethyl)-2,4(1H,3H)-pyrimidinedione;

3-{4-chloro-3-[2-(cyclopropylmethyl)-2H-tetrazol-5-yl]phenyl}-1-methyl-6-(trifluoromethyl)-2,4(1H,3H)-pyrimidinedione;

3-[3-(2-butyl-2H-tetrazol-5-yl)-4-chlorophenyl]-1-methyl-6-(trifluoromethyl)-2,4(1H,3H)-pyrimidinedione;

3-(4-chloro-3-{2-[(4-chlorophenoxy)methyl]-2H-tetrazol-5-yl}phenyl)-1-methyl-6-(trifluoromethyl)-2,4(1H,3H)-pyrimidinedione;

3-(4-chloro-3-{1-[(4-chlorophenoxy)methyl]-1H-tetrazol-5-yl}phenyl)-1-methyl-6-(trifluoromethyl)-2,4(1H,3H)-pyrimidinedione;

3-{4-chloro-3-[2-(4-chlorobenzyl)-2H-tetrazol-5-yl]phenyl}-1-methyl-6-(trifluoromethyl)-2,4(1H,3H)-pyrimidinedione;

3-{4-chloro-3-[1-(4-chlorobenzyl)-1H-tetrazol-5-yl]phenyl}-1-methyl-6-(trifluoromethyl)-2,4(1H,3H)-pyrimidinedione;

methyl 2-{2-chloro-5-[1,2,3,6-tetrahydro-3-methyl-2,6-dioxo-4-(trifluoromethyl)pyrimidin-1-yl]phenyl}-1,3-thiazole-4-carboxylate;

methyl (2-{2-chloro-5-[1,2,3,6-tetrahydro-3-methyl-2,6-dioxo-4-(trifluoromethyl)pyrimidin-1-yl]phenyl}-1,3-thiazol-4-yl)acetate.

3. A herbicidal composition containing, as active principle, an effective amount of one or more compounds having formula (I) according to claim 1 and a non-phytotoxic carrier.

4. The herbicidal composition according to claim 3, characterized in that the concentration of the active substance ranges from 1 to 90%.

5. A compound as defined in claim 1 wherein Q is 1,2,4-oxadiazolyl.

6. A compound as defined in claim 1 wherein Q is 5-methyl-1,2,4-oxadiazolyl.

* * * * *